(12) United States Patent
Castillo

(10) Patent No.: US 10,137,028 B2
(45) Date of Patent: Nov. 27, 2018

(54) EYEWEAR SYSTEM FOR SECURING LENS ON A USER'S NOSE AND DILATING USER'S NOSE

(71) Applicant: James D. Castillo, Los Alamos, CA (US)

(72) Inventor: James D. Castillo, Los Alamos, CA (US)

(*) Notice: Subject to any disclaimer, the term of this patent is extended or adjusted under 35 U.S.C. 154(b) by 5 days.

(21) Appl. No.: 15/071,459

(22) Filed: Mar. 16, 2016

(65) Prior Publication Data

US 2016/0193070 A1    Jul. 7, 2016

Related U.S. Application Data

(63) Continuation-in-part of application No. 14/979,009, filed on Dec. 22, 2015, which is a
(Continued)

(51) Int. Cl.
*A61F 5/08* (2006.01)
*A61F 9/02* (2006.01)

(52) U.S. Cl.
CPC .............. *A61F 5/08* (2013.01); *A61F 9/026* (2013.01); *A61F 9/029* (2013.01)

(58) Field of Classification Search
CPC .. A61F 5/08; A61F 5/56; A61M 29/00; A61B 17/24
See application file for complete search history.

(56) References Cited

U.S. PATENT DOCUMENTS

| 3,835,848 A | 9/1974 | Berner |
| 4,835,506 A | 5/1989 | Leupold |

(Continued)

FOREIGN PATENT DOCUMENTS

| CN | 1389185 | 1/2003 |
| JP | H10192412 | 7/1998 |

(Continued)

OTHER PUBLICATIONS

First Office Action of CN Application 201480075735.9, dated May 2, 2017, 9 pages.
(Continued)

*Primary Examiner* — Ashley Fishback
(74) *Attorney, Agent, or Firm* — Stetina Brunda Garred and Brucker

(57) ABSTRACT

A device for securing an eyewear lens to a nasal applique which results in nasal dilation. The device includes a base engageable with the eyewear lens. First and second pivot units are is coupled to the base pivotal about respective pivot axes. The pivot units collectively define a nose adjustment angle therebetween, with the nose adjustment angle being generally conformable to the user's nose. The first pivot unit and the second pivot unit are configured to interact with at least one nasal applique to magnetically couple the first pivot unit and the second pivot unit to the at least one nasal applique. The magnetic coupling between the first pivot unit and the second pivot unit and the at least one nasal applique imparts a dilating force on the user's nose to dilate the nasal passageway when the at least one nasal applique is attached to the user's nose.

17 Claims, 16 Drawing Sheets

Related U.S. Application Data continuation-in-part of application No. 14/799,192, filed on Jul. 14, 2015, which is a continuation-in-part of application No. 14/622,448, filed on Feb. 13, 2015, now Pat. No. 9,283,106, which is a continuation-in-part of application No. 14/502,348, filed on Sep. 30, 2014, now Pat. No. 9,675,493.

(60) Provisional application No. 61/918,826, filed on Dec. 20, 2013, provisional application No. 61/937,018, filed on Feb. 7, 2014.

(56) References Cited

U.S. PATENT DOCUMENTS

| | | | |
|---|---|---|---|
| 4,886,349 A | 12/1989 | Willis | |
| 5,533,503 A | 7/1996 | Doubek et al. | |
| 5,566,503 A | 7/1996 | Doubek et al. | |
| 5,682,222 A * | 10/1997 | Chao | G02C 5/2254 351/111 |
| 5,719,655 A | 2/1998 | Peschel et al. | |
| 5,913,873 A | 6/1999 | Blach et al. | |
| 5,957,126 A | 9/1999 | Neeser | |
| 6,006,746 A | 12/1999 | Karell | |
| 6,033,422 A | 3/2000 | Blach et al. | |
| 6,352,548 B1 | 3/2002 | Blach et al. | |
| 6,533,412 B1 | 3/2003 | Wang et al. | |
| 6,540,349 B1 | 4/2003 | Liesegang | |
| 6,648,471 B1 | 11/2003 | Dalrymple et al. | |
| 6,676,681 B1 | 1/2004 | Blach et al. | |
| 6,823,864 B2 | 11/2004 | Blach et al. | |
| 7,091,634 B2 | 8/2006 | Yi et al. | |
| 7,118,210 B2 | 10/2006 | Landers | |
| 7,793,661 B2 | 9/2010 | Macken | |
| D639,762 S | 6/2011 | Brogden et al. | |
| D644,324 S | 8/2011 | Brunner et al. | |
| D644,325 S | 8/2011 | Brunner et al. | |
| 8,042,542 B2 | 10/2011 | Ging et al. | |
| 8,292,427 B2 | 10/2012 | Zelazowski | |
| 8,459,254 B1 | 6/2013 | Jassir et al. | |
| D696,400 S | 12/2013 | Brogden et al. | |
| D701,957 S | 4/2014 | Brunner et al. | |
| D703,318 S | 4/2014 | Brunner et al. | |
| 2002/0029408 A1 | 3/2002 | Lindahl | |
| 2003/0000521 A1 | 1/2003 | Beaudry | |
| 2007/0105824 A1 | 5/2007 | Erickson-Miller et al. | |
| 2007/0252946 A1 | 11/2007 | Welchel | |
| 2008/0097517 A1 | 4/2008 | Holmes et al. | |
| 2008/0119885 A1 | 5/2008 | Yazdi | |
| 2009/0183734 A1 | 7/2009 | Kwok et al. | |
| 2009/0188023 A1 | 7/2009 | Hsu | |
| 2010/0309425 A1 | 12/2010 | Zelazowski | |
| 2011/0000483 A1 | 1/2011 | Matthias et al. | |
| 2011/0043749 A1 * | 2/2011 | Alley | G02C 11/00 351/111 |
| 2012/0024639 A1 * | 2/2012 | Castro | B60T 7/16 188/24.22 |
| 2012/0036607 A1 | 2/2012 | Beliveau | |
| 2012/0172923 A1 | 7/2012 | Fenton et al. | |
| 2014/0296904 A1 | 10/2014 | Andre | |
| 2014/0375946 A1 | 12/2014 | Rochford et al. | |
| 2015/0001014 A1 * | 1/2015 | Noborio | B62L 1/005 188/73.31 |
| 2015/0173933 A1 | 6/2015 | Castillo | |
| 2015/0173934 A1 | 6/2015 | Castillo | |
| 2017/0106222 A1 * | 4/2017 | Mayer | A63B 21/0051 |

FOREIGN PATENT DOCUMENTS

| | | |
|---|---|---|
| JP | 2009-535079 | 10/2009 |
| KR | 200404740 | 12/2005 |
| WO | WO2002/003125 | 1/2002 |

OTHER PUBLICATIONS

Summary of First Office Action of CN Application 2014800757359, dated May 2, 2017, 5 pages.

International Search Report and Written Opinion of International Application No. PCT/US15/67530, dated May 16, 2016, 11 pages.

International Search Report and Written Opinion of International Application No. PCT/US2016/022637, dated Jun. 9, 2016, 10 pages.

International Search Report and Written Opinion for International Application No. PCT/US14/69817, dated Mar. 11, 2015, 11 pages.

European Patent Office, extended European search report for Application No. EP 14871764, dated Jul. 7, 2017, 10 pages.

Patent Cooperation Treaty, International Preliminary Report on Patentability for Application No. PCT/US16/22637, dated Aug. 3, 2017, 9 pages.

Australian Government IP Australia, Examination report No. 1 for standard patent application, dated Oct. 24, 2017, 5 pages.

Office Action for corresponding Japanese Patent Application No. 2016-560622 with English translation, dated Nov. 1, 2017, 5 pages.

International Search Report and Written Opinion for International Application No. PCT/US 17/45688, dated Oct. 31, 2017, 11 pages.

* cited by examiner

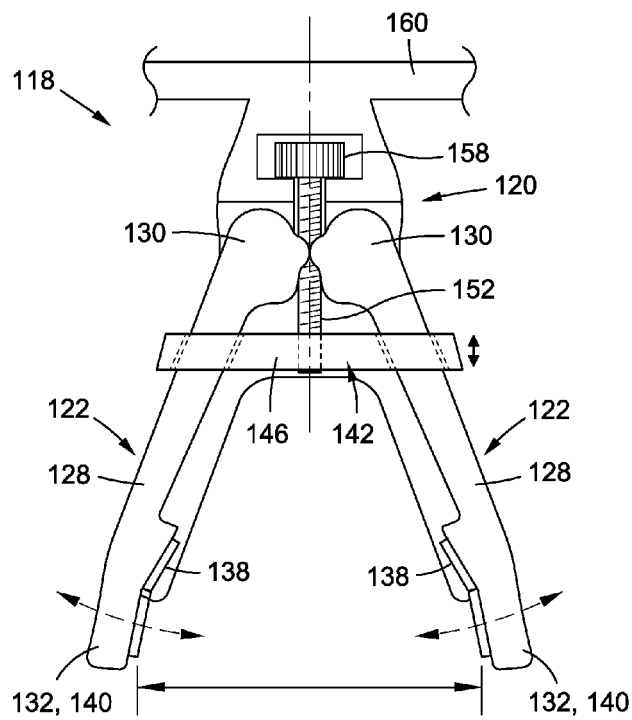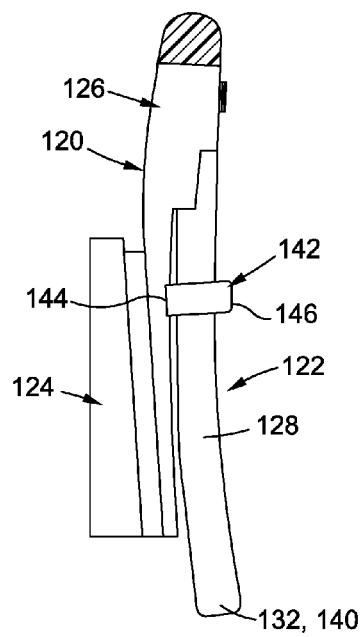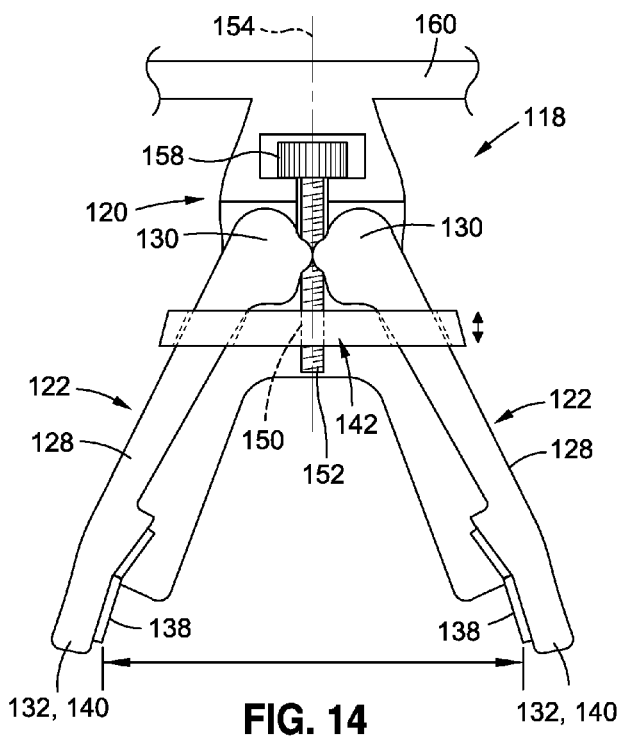

EYEWEAR SYSTEM FOR SECURING LENS ON A USER'S NOSE AND DILATING USER'S NOSE

CROSS-REFERENCE TO RELATED APPLICATIONS

This application is a continuation-in-part of U.S. patent application Ser. No. 14/979,009, filed Dec. 22, 2015, which is a continuation-in-part of U.S. patent application Ser. No. 14/799,192, filed Jul. 14, 2015, which is a continuation-in-part of U.S. patent application Ser. No. 14/622,448, filed Feb. 13, 2015 and published as United States Patent Application Publication No. 2015/0173934, which is a continuation-in-part of U.S. patent application Ser. No. 14/502,348, filed Sep. 30, 2014 and published as United States Patent Application Publication No. 2015/0173933, which claims the benefit of U.S. Provisional Application No. 61/918,826, filed Dec. 20, 2013, and U.S. Provisional Application No. 61/937,018, filed Feb. 7, 2014, the contents of each of the foregoing applications being expressly incorporated herein by reference.

STATEMENT RE: FEDERALLY SPONSORED RESEARCH/DEVELOPMENT

Not Applicable

BACKGROUND

1. Technical Field

The present disclosure relates generally to components for breathing enhancement, and more specifically to a system including a nasal applique wearable on a user's nose and a lens retaining device magnetically attractable to the nasal applique for securing the lens to the user's nose and dilating the user's nasal passageway.

2. Description of the Related Art

It is readily understood that breathing is important when playing sports or partaking in physical competition due to the increased demand for oxygen by the body. Breathing may be achieved by drawing air into the body through an individual's nostrils and/or through the individual's mouth. However, in some instances, it is preferable to breathe almost exclusively through the nostrils, as there may be a downside to breathing through one's mouth. Along these lines, breathing through the mouth may lead to rapid water loss and heat loss, both of which increase the likelihood of exercise-induced asthma.

It is also understood that eyewear is commonly used when participating in many sports and activities. Such eyewear may include sunglasses, protective eyewear, or vision-enhancing (e.g., prescription) eyewear. However, at the very least, most eyewear is not adapted to improve the ability of the wearer's breathing, and in some instance, may actually hinder the wearer's breathing by compressing the user's nose and constricting the nasal passageways.

Accordingly, there is a need in the art for a device which can be used with an eyewear lens or lenses for enhancing the wearer's ability to breathe through the wearer's nasal passage while wearing the eyewear lens(es). Various aspects of the present invention address this particular need, as will be discussed in more detail below.

BRIEF SUMMARY

In accordance with one embodiment of the present disclosure, there is provided a device for securing an eyewear lens to at least one nasal applique attachable to a user's nose which results in dilation of a nasal passageway. The device includes a base configured to be engageable with the eyewear lens. A first pivot unit is coupled to the base and is pivotable relative to the base about a first pivot axis. A second pivot unit is coupled to the base and is pivotable relative to the base about a second pivot axis spaced from, and generally parallel to the first pivot axis. The first pivot unit and the second pivot unit are configured to interact with at least one nasal applique to magnetically couple the first pivot unit and the second pivot unit to the at least one nasal applique. The magnetic coupling between the first pivot unit and the second pivot unit and the at least one nasal applique imparts a dilating force on the user's nose to dilate the nasal passageway when the at least one nasal applique is attached to the user's nose.

The device may include a guide member coupled to the first pivot unit and the second pivot unit, with the guide member being moveable relative to the base and movement of the guide member relative to the base causing pivotal movement of the first pivot unit and the second pivot unit relative to the base.

The guide member may include a pair of grooves formed therein, with the first and second pivot units being received within respective ones of the pair of grooves. The guide member may include a camming surface which interfaces with the first pivot unit and the second pivot unit, with the camming surface being sized and configured to transform translational movement of the guide member into pivotal movement of the first pivot unit and the second pivot unit. The device may further include an adjustment shaft coupled to the base and the guide member, with the guide member being translatable along the adjustment shaft. The guide member and adjustment shaft may be configured such that the guide member is translatable along the adjustment shaft in response to rotation of the adjustment shaft about a rotation axis. The device may additionally include an adjustment knob coupled to the adjustment shaft and adapted to enable manually controlled rotation of the adjustment shaft about the rotation axis.

The first pivot unit may include a first gear portion and the second pivot unit may include a second gear portion cooperatively engaged with the first gear portion to facilitate geared pivotal motion of the first pivot unit relative to the second pivot unit. The device may further comprise an eyewear frame including a forward frame element and a pair of arms pivotally coupled to the forward frame element, with the base being integrally coupled to the forward frame element.

The base may include a bridge element having a lens receiving channel adapted to receive the eyewear lens. The base may include a hinge element coupled to the bridge element and have a first hinge portion and a second hinge portion, with the first pivot unit being coupled to the hinge element at the first hinge portion and the second pivot unit being coupled to the hinge element at the second hinge portion.

The device may include a retaining member coupled to the base and adapted to engage with the user's nose to retain the device on the user's nose.

The first pivot unit may include a first pivot arm pivotally coupled to the base and the second pivot unit may include a second pivot arm pivotally coupled to the base. At least one magnet may be coupled to the first pivot arm, and at least one magnet may be coupled to the second pivot arm. A first pair of magnets may be coupled to the first pivot arm and angularly offset from each other and a second pair of magnets may be coupled to the second pivot arm and angularly offset from each other. A first pad may be coupled to the first pivot arm and a second pad may be coupled to the second pivot arm. The first pad may be translatable along the first pivot arm and the second pad may be translatable along the second pivot arm. The first pivot arm and the second pivot arm may be positioned on opposite sides of a central axis. A first magnet may be coupled to the first pivot arm and have a first magnet inward surface facing toward the central axis. A second magnet may be coupled to the second pivot arm and have a second magnet inward surface facing toward the central axis. The first pad may have a first pad inward surface facing toward the central axis and the second pad may have a second pad inward surface facing toward the central axis. The first magnet inward surface may be offset from the first pad inward surface and the second magnet inward surface may be offset from the second pad inward surface. The first magnet inward face may be generally parallel with the first pad inward face and the second magnet inward face may be generally parallel with the second pad inward face. The first pad may be detachably coupled to the first pivot arm and the second pad may be detachably coupled to the second pivot arm.

According to another embodiment, there is provided a system for attaching an eyewear lens to a user's nose and dilating the user's nose. The system comprises at least one nasal applique including a base layer and a metallic element coupled to the base layer, with the base layer configured to be attachable to the user's nose. The system further includes an eyewear securing device operatively connectable to the at least one nasal applique. The eyewear securing device includes a base configured to be engageable with the eyewear lens. A first pivot unit is coupled to the base and is pivotal relative to the base about a first pivot axis. A second pivot unit is coupled to the base and is pivotal relative to the base about a second pivot axis spaced from, and generally parallel to the first pivot axis. The first pivot unit and the second pivot unit collectively define a nose adjustment angle therebetween, with the nose adjustment angle being generally conformable to the user's nose. The first pivot unit and the second pivot unit are configured to interact with at least one nasal applique to magnetically couple the first pivot unit and the second pivot unit to the at least one nasal applique. The magnetic coupling between the first pivot unit and the second pivot unit and the at least one nasal applique imparts a dilating force on the user's nose to dilate the nasal passageway when the at least one nasal applique is attached to the user's nose.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which:

FIG. 12 is a side view of the third embodiment of the eyewear lens mounting device;

FIG. 13 is a rear view of the third embodiment of the eyewear lens mounting device in a narrow configuration;

FIG. 14 is a rear view of the third embodiment of the eyewear lens mounting device in a wide configuration;

Common reference numerals are used throughout the drawings and the detailed description to indicate the same elements.

DETAILED DESCRIPTION

The detailed description set forth below in connection with the appended drawings is intended as a description of certain embodiments of a system for simultaneously positioning an eyewear lens on a user's nose and dilating the user's nose to enhance airflow therethrough and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Figure 1:
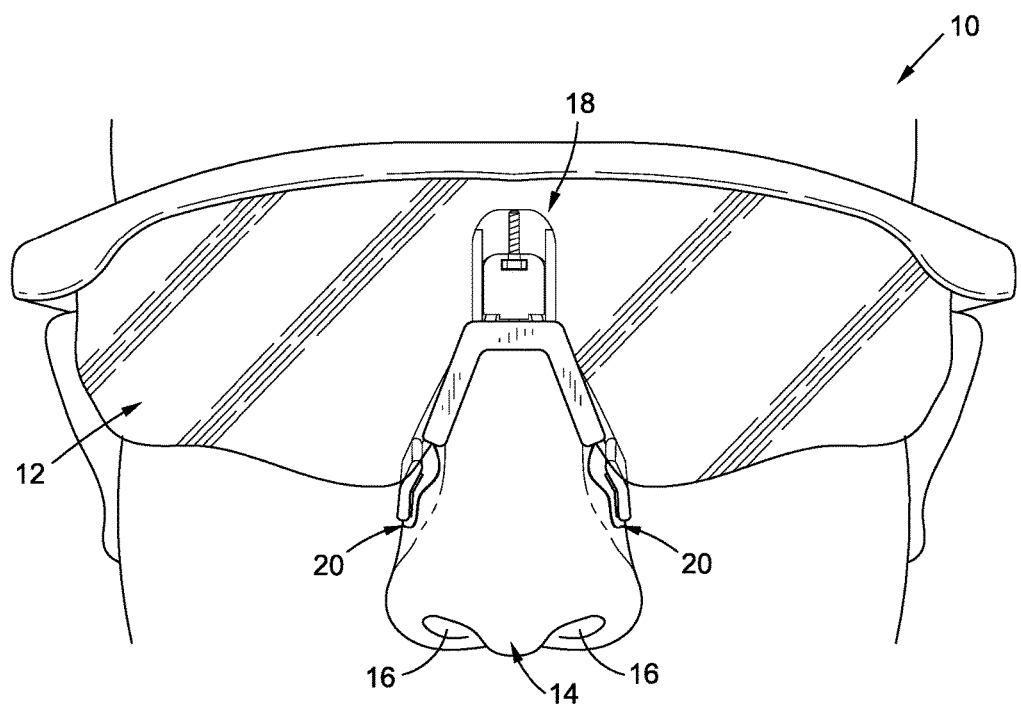
FIG. 1 is a front view of a first embodiment of a system including an eyewear lens mounting device and a pair of nasal appliques.

Referring now to FIG. 1 and according to one embodiment of the present disclosure, there is provided a system 10 for simultaneously securing an eyewear lens 12 to a user's nose 14 and dilating the user's nose 14 by imparting a dilating force on a region of the nose 14 defining the nasal passageway 16. As will be described in more detail below, the system 10 utilizes magnetic force to connect a lens mounting device 18 to one or more nasal appliques 20 which are adhered to the user's nose 14. The magnetic force at least partially maintains the lens mounting device 18 on the user's nose 14, with the lens mounting device 18 being adapted to engage with the eyewear lens 12 so as to position the eyewear lens 12 in a conventional position in front of the user's eyes. The magnetic force also "pulls" or biases the applique(s) 20 toward the lens mounting device 18 to dilate the nasal passageways 16.

Figure 2:
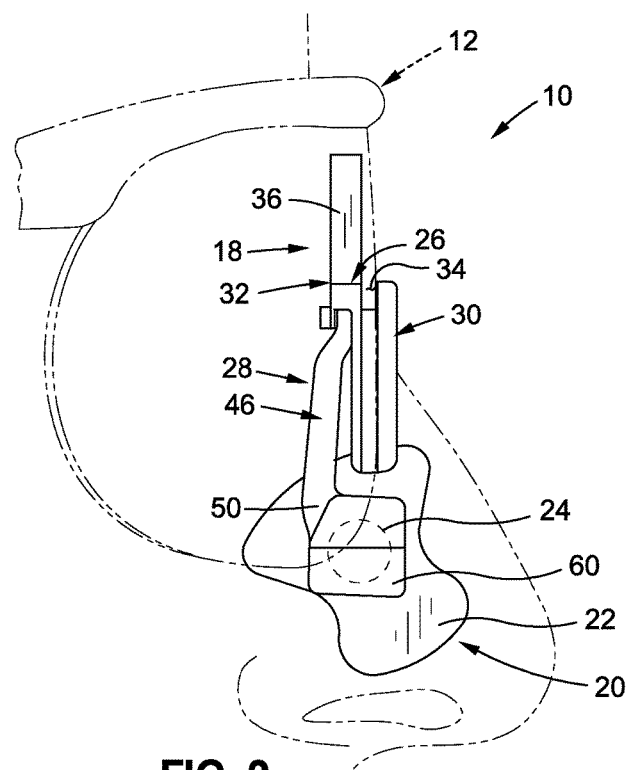
FIG. 2 is a side view of the first embodiment of the eyewear lens mounting device.
Figure 3:
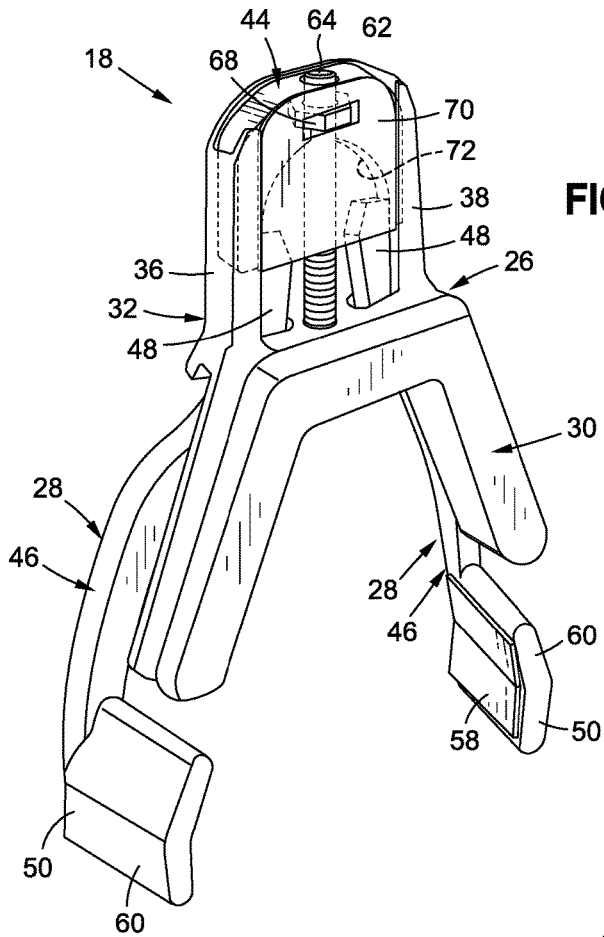
FIG. 3 is a front upper perspective view of the first embodiment of the eyewear lens mounting device.
Figure 4:
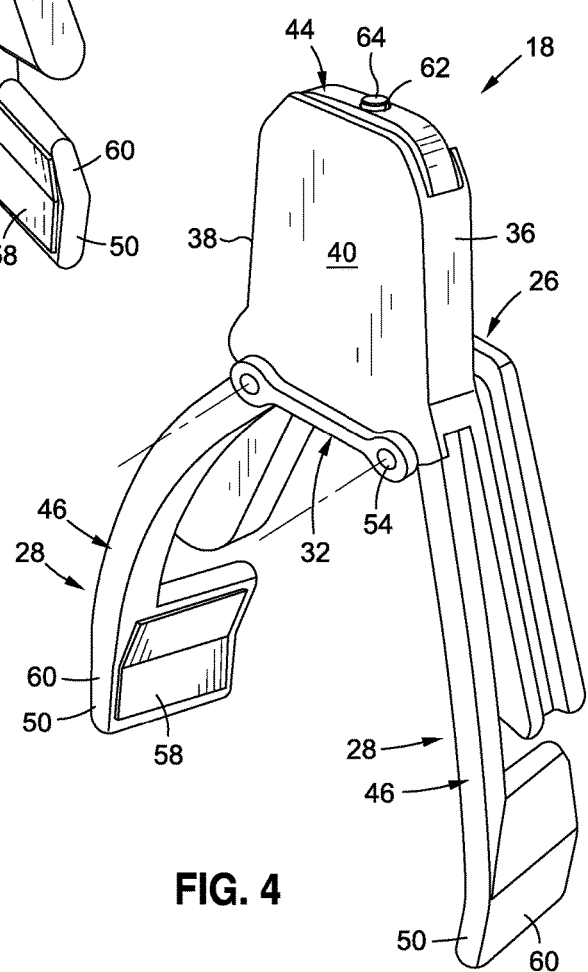
FIG. 4 is a rear upper perspective view of the first embodiment of the eyewear lens mounting device.
Figure 5:
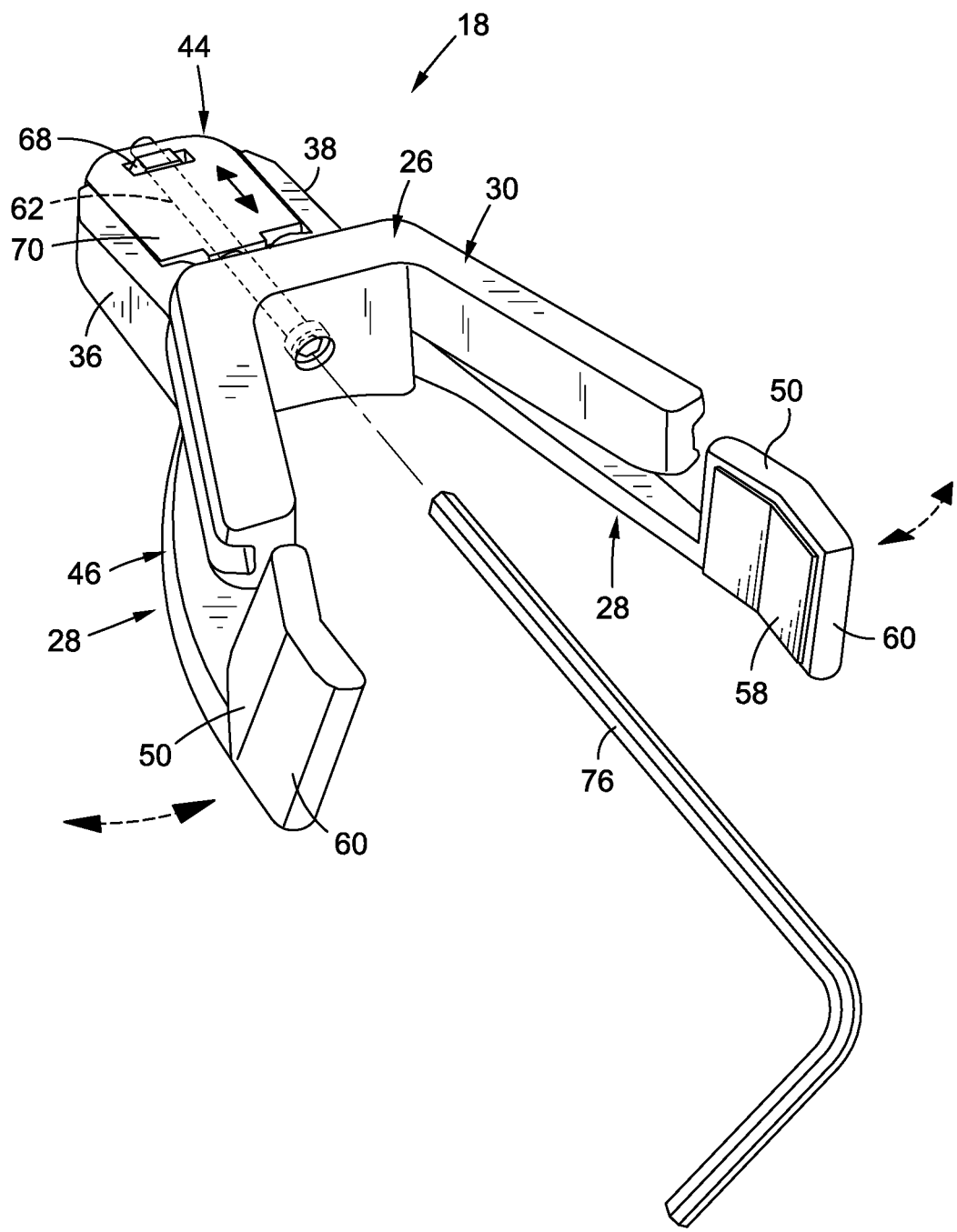
FIG. 5 is a bottom perspective view of the first embodiment of the eyewear lens mounting device along with an adjustment tool.

The system 10 shown in FIGS. 1 and 2 includes a pair of nasal appliques 20, with each nasal applique 20 generally including a flexible body 22 and the metallic element 24 coupled to the flexible body 22. The flexible body 22 is configured to be attached to a lateral region of the user's nose 14, with the flexible body 22 being capable of bending/flexing to conform to the unique anatomy of the user's nose 14. According to one embodiment, the flexible body 22 includes an adhesive disposed on an outer surface thereof to enable selective attachment of the applique 20 to the nose 14. A peel-away layer may be coupled to the flexible body 22 and cover the adhesive to preserve the adhesive until the applique 20 is to be used.

According to one embodiment, and when viewed in from the perspective depicted in FIG. 2, the flexible body 22 defines an outer periphery that is generally of the shape of an hour-glass or butterfly. In this respect, the outer periphery includes a pair of enlarged end portions separated by a narrow middle portion having a pair of opposed concave edges. The generally hour-glass configuration of the outer periphery may enable the flexible body 22 to more easily conform to the unique anatomy of the user's nose 14. For instance, one end portion of the flexible body 22 may extend onto the "ala of the nose," e.g., the rounded eminence extending around the nostril, the middle portion of the flexible body 22 may extend over the alar crease, and the remaining end portion of the flexible body 22 may extend on an adjacent region of the nose 14. The applique 20 shown in FIG. 2 is designed to be used on either side of the nose, although it is contemplated that the appliques 20 may be specifically configured for use on either the left-side or right-side of the nose 14. In that instance, the cutout defined by the concave edge on the applique 20, which would accommodate the crease on the nose 14, would be on the side of the applique 20 closest to the user's cheek, and away from the ridge of the nose 14.

According to one embodiment, the flexible body 22 is a composite structure including a pair of outer layers with the metallic element 24 being captured between the outer layers. The layers may be secured to each other via adhesive, lamination, or other means known in the art. The metallic element 24 is configured to interact with a magnet when the magnet is remotely positioned adjacent the nose 14 and the flexible body 22 is attached to the nose 14. In the case of system 10, the magnet which interacts with the metallic element 24 is part of the lens mounting device 18, which will be described in more detail below. The metallic element 24 is positioned such that at least a portion of the flexible body 22 extends radially outward beyond the metallic element 24 to define a flexible peripheral portion.

According to one embodiment, the metallic element 24 includes a convex surface defining a "domed" or arcuate configuration to enhance magnetic engagement with the remotely located magnet. In this regard, flat-to-flat attachment between the magnet and the metallic element 24 may create uncomfortable torque on the user's nose 14. Thus, by creating a domed engagement surface on the metallic element 24, such uncomfortable torque may be avoided. Furthermore, the convex surface defines a suitable structure which does not inhibit motion of the magnet thereover, and instead, allows the magnet to move or float along during engagement between the applique 20 and the magnet. In particular, the magnet may move along at least one axis, and more preferably along at least two axes, relative to the metallic element 24 while the metallic element 24 remains magnetically engaged with the magnet.

The domed or arcuate surface may be positioned opposite a generally planar surface of the flexible body 22, such as substantially parallel to a flexible body plane defined by the flexible body 22. It is understood that the outer periphery of the metallic element 24 may be any shape, including circular, oval, quadrangular, etc. The advantages of the convex engagement between the metallic element 24 and the corresponding magnet may also be effectuated through the use of an arcuate or dome shaped magnet. In this respect, the metallic element 24 and/or the magnet may have an arcuate or rounded surface.

According to one embodiment, the flexible body 22 includes at least one perforation (not shown) extending through the flexible body 22 to ventilate the user's skin residing under the applique 20 to prevent sweat from building up under the applique 20. Along these lines, a buildup of sweat between the applique 20 and the user's skin could diminish the ability of the adhesive to effectively secure the applique 20 to the user's nose 14. Thus, by incorporating the perforation(s), the sweat can evaporate or flow away from the user's skin to more effectively maintain adhesion between the applique 20 and the user's nose 14.

For more information regarding nasal appliques 20, please refer to U.S. patent application Ser. Nos. 14/799,192, 14/622,448, (published as United States Patent Application Publication No. 2015/0173934), U.S. patent application Ser. No. 14/502,348 (published as United States Patent Application Publication No. 2015/0173933), the contents of each of which being expressly incorporated herein by reference.

Furthermore, although the exemplary embodiment includes a pair of nasal appliques 20, it is understood that other embodiments of the system 10 may include a single applique 20, while in other embodiments, the system 10 may include more than a pair of nasal appliques 20. In this respect, the scope of the present disclosure is not limited to a particular number of nasal appliques 20.

Turning now to the lens mounting device 18, such device 18 generally includes a base 26 and a pair of pivot units 28 pivotally coupled to the base 26. The lens mounting device 18 is adjustable via the pivot units 28 to conform to the size and shape of the user's nose 14, as well as to adjust the magnitude of the dilating force on the user's nose, as will be described in more detail below.

According to one embodiment, the base 26 is comprised of a bridge element 30 adapted to receive the eyewear lens 12 and a hinge element 32 adapted to pivotally engage with the pivot units 28. The bridge element 30 and hinge element 32 shown in the exemplary embodiment are integral with each other, although it is understood that the bridge element 30 and hinge element 32 may be separate components which cooperate with each other.

The bridge element 30 includes a lens receiving channel 34 adapted to receive the eyewear lens 12. The bridge element 30 includes a pair of bridge element arms which intersect at an apex and are adapted to extend along opposing lateral regions of the user's nose 14 when the base 26 is coupled to the user's nose 14. The lens receiving channel 34 is formed by a forward wall and a rearward wall, with the lens receiving channel 34 being positioned therebetween, and extending along the pair of bridge element arms. The width of the lens receiving channel 34 (e.g., the distance between the forward wall and the rearward wall) generally corresponds to the thickness of the eyewear lens 12 so as to securely retain the eyewear lens 12 therein.

The hinge element 32 is pivotally coupled to the first and second pivot units 28 and includes a first sidewall 36, a second sidewall 38, and a main wall 40 extending between the first sidewall 36 and the second sidewall 38. The first sidewall 36, second sidewall 38, and main wall 40 may collectively define a cavity 42 (see FIG. 7), which receives a guide member 44, which will be described in more detail below.

Each pivot unit 28 includes a pivot arm 46 pivotally coupled to the hinge element 32 and including a first end portion 48 and an opposing second end portion 50. In the exemplary embodiment, each pivot arm 28 includes a pivot bore 52 which is aligned with a hinge bore 54 formed on the hinge element 32, with a pivot pin extending through the pivot bore 52 and hinge bore 54 to pivotally couple the pivot arm 46 to the hinge element 32. The pivot arms 28 are positioned such that the first end portion 48 of each pivot arm 46 extends into the cavity 42 adjacent a respective sidewall 36, 38 of the hinge element 32. The first end portion 48 of each pivot arm 28 defines an arm camming surface 56 which is specifically configured and adapted to interface with the guide member 44, as will be described in more detail below.

The second end portion 50 of each pivot arm 28 is coupled to at least one magnet 58, and preferably a pair of magnets 58. In the exemplary embodiment, each pivot arm 46 includes a magnet holder 60, which may result in an enlarged form factor at the second end portion 50 of the pivot arm 46. Each magnet holder 60 is sized and configured to engage with one, and more preferably, a pair of magnets 58. Each magnet 58 includes an exposed surface, which faces away from the corresponding magnet holder 60.

According to one embodiment, a pair of magnets 58 is coupled to each magnet holder 60, wherein the exposed surfaces of the magnets 58 are angularly offset from each other to define a shallow "V" shape. The angularly offset configuration of the magnets 58 mitigates face-to-face magnetic engagement with the metallic element 24 of the nasal applique 20, and thus, reduces torque being applied to the user's nose as the nasal applique 20 moves relative to the magnets 58, or is urged to move relative to the magnets 58.

The pivot units 28 are configured to interact with the nasal appliques 20 to magnetically couple the pivot units 28 to the nasal appliques 20. The magnetic coupling between the pivot units 28 and the nasal appliques 20 imparts a dilating force on the user's nose 14 to dilate the nasal passageway 16. In this respect, the appliques 20 are specifically configured and adapted to selectively transition between an "ON" state and an "OFF" state, by selectively donning or removing the lens mounting device 18 from the user's nose 14. In particular, if the lens mounting device 18 is placed on the user's nose 14, thereby placing the magnets 58 in close proximity to the appliques 20 residing on the user's nose 14, the metallic elements 24 are drawn toward a respective magnet 58 (or a respective pair of magnets 58), thereby imparting the dilating force on the nose 14. In contrast, if the lens mounting device 18 is removed from the user's nose 14, and thus, the magnets 58 are no longer in close proximity to the user's nose 14, the metallic elements 24 are not drawn away from the user's nose 14, and thus, no dilating force is imparted on the nose 14 by the appliques 20. The ability to selectively transition between ON and OFF states without requiring removal of the appliques 20 from the user is a significant benefit, as it allows a user to place the appliques 20 on the nose 14 at the beginning of an athletic event, and keep the appliques 20 on the nose 14 throughout the duration of the athletic event, while allowing the user to selectively transition the appliques 20 between the ON and OFF states. Such ability to transition between ON and OFF states is a significant departure from existing nasal "strips" which use a spring-biased metal strip to open a user's nasal passageway. The conventional nasal strips continuously apply a dilating force on the user's nose the entire time the nasal strip is coupled to the nose. In this regard, the conventional nasal strip does not include the ability to seamlessly transition between ON and OFF states based on the proximity of a magnet.

According to one embodiment, the nasal appliques 20 and the magnets 58 are configured to allow for relative movement between the appliques 20 and magnets 58 while the appliques 20 are magnetically coupled to the magnets 58. For instance, the domed or arcuate configuration of the metallic element 24 allow for movement of the magnet(s) 58 over the surface of the metallic element 24. In particular, the magnet(s) 58 may move along at least one axis, and preferably along at least two axes relative to the metallic element 24 when the magnet 58 is magnetically held adjacent to the metallic element 24. Such relative movement between the nasal appliques 20 and the magnets 58 may result from increased activity by the wearer. Such movement of the magnet(s) 58 over the surface of the metallic element 24 facilitates removal or disengagement of the magnets 58 (and the entire lens mounting device 18) from the appliques 20, so long as the user applies sufficient force to overcome the magnetic attraction. In this regard, since the coupling between the lens mounting device 18 and the appliques 20 may be exclusively achieved via magnetic coupling, and may not rely on any non-magnetic coupling, disengagement of the lens mounting device 18 from the appliques 20 is relatively simple.

Pivotal movement of the pivot units 28 is controlled via the guide member 44, which translates within the cavity 42 formed by the hinge element 32 and is coupled to the pivot units 28 in a manner which transforms the translational movement of the guide member 44 into pivotal movement of the pivot units 28. The outer configuration of the guide member 44 is complimentary in shape to the cavity 42, and includes a first side portion that is complimentary to the first sidewall 36, and a second side portion that is complimentary to the second sidewall 38. The guide member 44 further includes a central bore 62 formed therein which is sized and configured to receive an adjustment shaft 64, which rotates about a rotation axis 66. The guide member 44 and adjustment shaft 64 are cooperatively configured to transform rotational movement of the adjustment shaft 64 into axial movement of the guide member 44. In the exemplary embodiment, the guide member 44 includes a nut 68 coupled to a guide body 70, wherein the nut 68 is received within a slot formed within the guide body 70. The internal threads of the nut 68 engage with the external threads on the adjustment shaft 64 so that as the adjustment shaft 64 rotates in a first rotational direction, the nut 68 and guide body 70 move relative to the base 26 along the adjustment shaft 64 (and the rotation axis 66) in a first axial direction, and as the adjustment shaft 64 rotates in an opposing second rotational direction, the nut 68 and guide body 70 move along the adjustment shaft 64 in an opposing second axial direction. Thus, by rotating the adjustment shaft 64, the guide member 44 can move relative to the base 26. It is understood that in other implementations, the guide member 44 may be threaded to directly engage with the adjustment shaft 64, and in such implementations, the guide member 44 may not include a nut. It is contemplated that the guide member 44 may be fabricated out of plastic, metal, or other materials known in the art.

Figure 6:
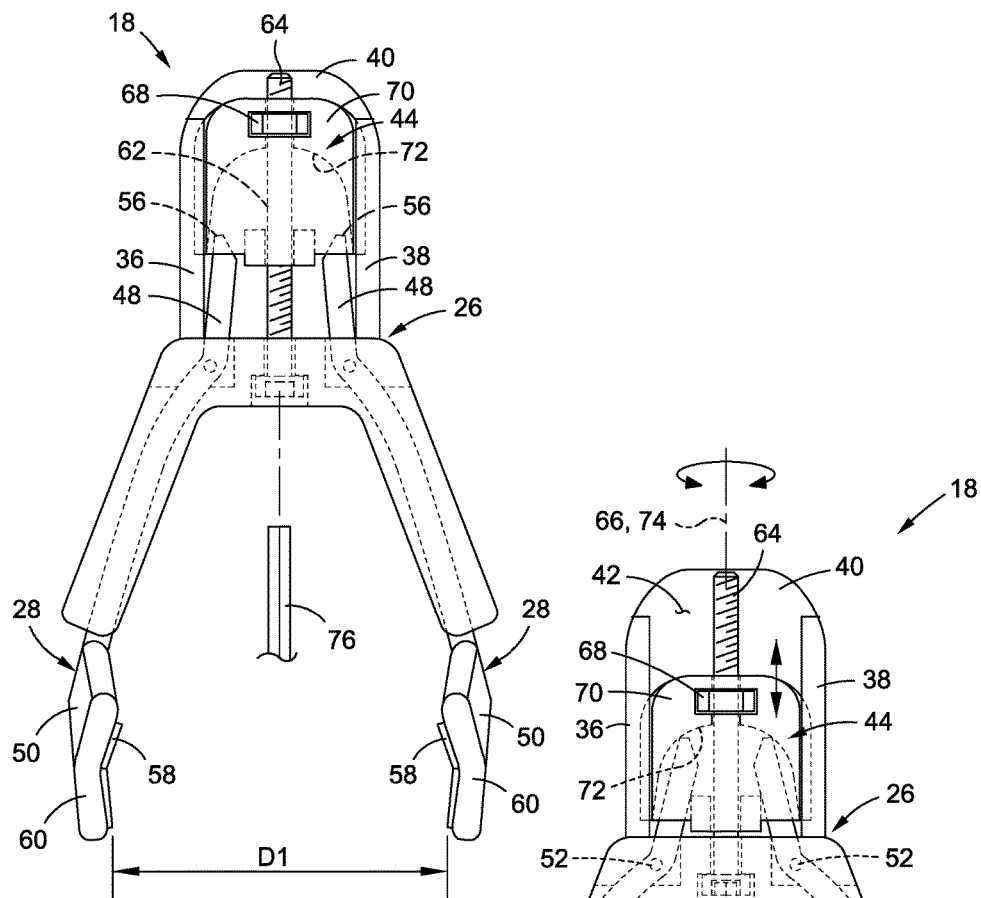
FIG. 6 is a front view of the first embodiment of the eyewear lens mounting device in a narrow configuration.
Figure 7:
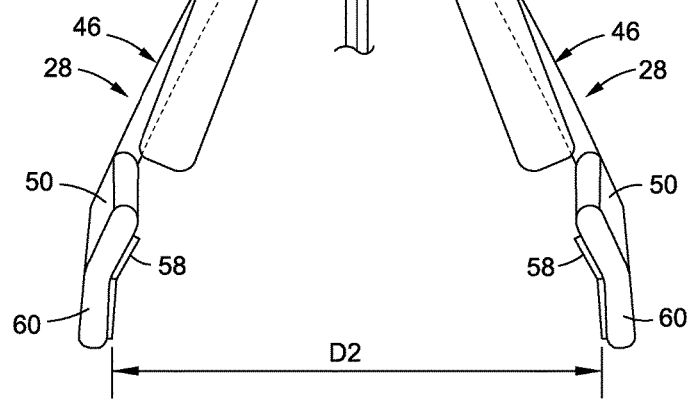
FIG. 7 is a front view of the first embodiment of the eyewear lens mounting device in a wide configuration.

The guide member 44 includes a guide camming surface 72 which interfaces with the pivot units 28 and is the portion of the guide member 44 that is sized and configured to transform translational movement of the guide member 44 into pivotal movement of the pivot units 28. As shown, the guide camming surface 44 is an arcuate surface that interfaces with both arm camming surfaces 56 of the pivot arms 46. The arcuate nature of the guide camming surface 44 creates movement of the respective ends of the pivot arms 46 along an axis that is generally perpendicular to the guide member translation axis 74. In the perspective shown in FIGS. 6 and 7, the guide member 44 is arranged such that the guide camming surface 72 defines an inverted "U" shape, with the open end of the "U" facing downward and being below the closed end of the "U." Each arm camming surface 56 is adapted to interface with a respective side of the "U." When the arms 46 are located at the open end of the "U," the pivot units 28 are in a narrow configuration, with the distance between opposed magnets 58 being $D_1$, as shown in FIG. 6. However, as the guide member 44 transitions from the location shown in FIG. 6 to the location shown in FIG. 7, the arm camming surfaces 56 move along the guide camming surface 72 toward the closed end of the "U." The arcuate configuration of the guide camming surface 72 causes the ends of the pivot units 28 to move toward the guide translation axis 74, and thus, toward each other, which results in the pivot units 28 assuming a wide configuration, as shown in FIG. 7, with the distance between opposed magnets 58 being $D_2$, which is larger than $D_1$. As the pivot units 28 transition from the narrow configuration toward the wide configuration, the distance between the second end portions 50 of the pivot arms 46 increases, as does the distance between the pairs of magnets 58. Conversely, as the pivot units 28 transition from the wide configuration toward the narrow configuration, the distance between the second end portions 50 of the pivot arms 46 decreases, as does the distance between the pairs of magnets 46.

The guide camming surface 72 is selectively transitioned between the narrow configuration and the wide configuration to adjust the dilating force applied to the user's nose. In particular, the wider the second end portions 50 of the pivot arms 46 are (e.g., the more space between the first and second pairs of magnets 58), the greater the magnitude of the dilating force applied to the user because the nasal appliques 20 are "pulled" or displaced toward the magnets 58 by a greater distance. Conversely, the magnitude of the dilating force may be reduced by transitioning the pivot units 28 to the narrow configuration, to lessen the distance by which the nasal appliques 20 are displaced.

As noted above, movement of the guide member 44 is associated with rotation of the adjustment shaft 64. According to one embodiment, a tool 76 is used to rotate the adjustment shaft 64. In this respect, the adjustment shaft 64 may have a socket or configuration complimentary in shape to the tool. For instance, the adjustment shaft 64 may be configured to engage with an allen wrench, screwdriver, or other mechanical tool known in the art. It is also contemplated that the adjustment shaft 64 may be configured to extend to a location which allows for manual adjustment thereof.

Figure 8:
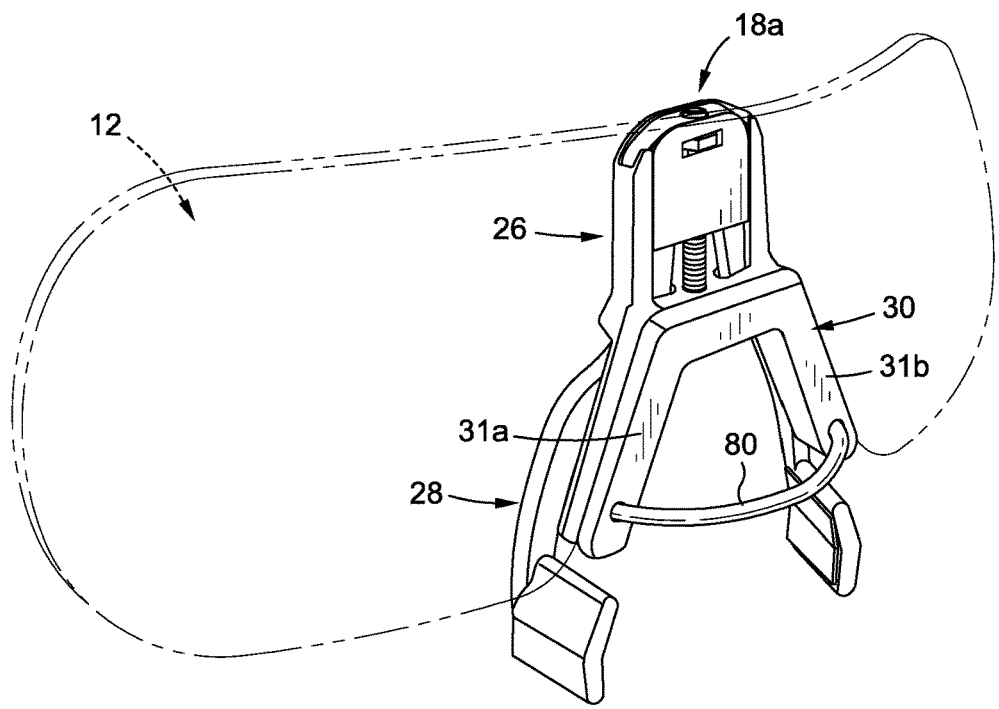
FIG. 8 is an upper perspective view of a second embodiment of an eyewear lens mounting device.
Figure 9:
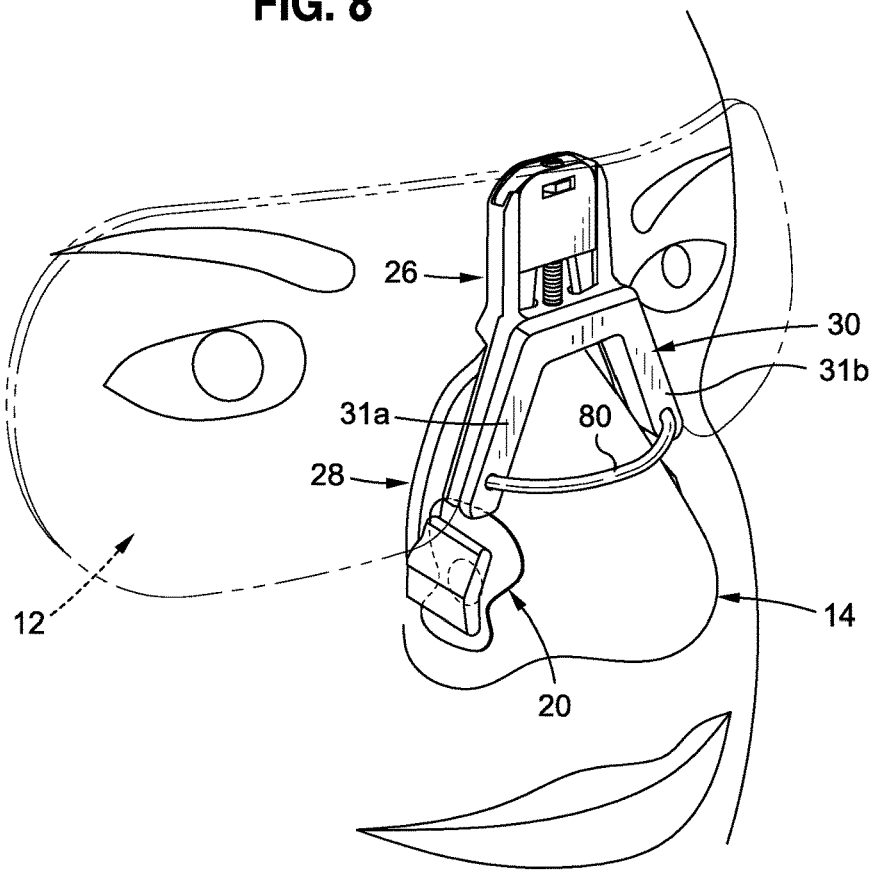
FIG. 9 is an upper perspective view of the second embodiment of the eyewear lens mounting device shown in use on a wearer.
Figure 10:
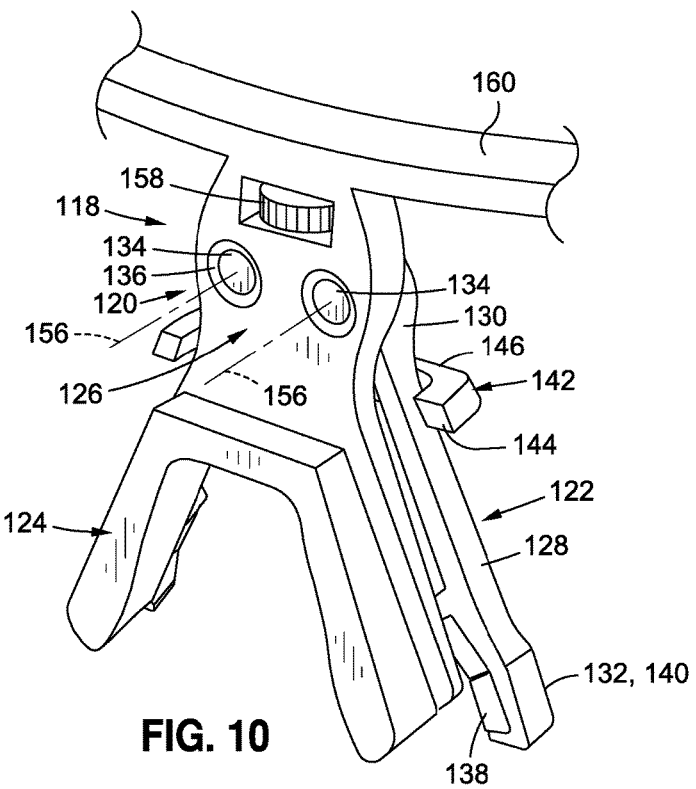
FIG. 10 is a front upper perspective view of a third embodiment of an eyewear lens mounting device integrated into an eyewear frame.
Figure 11:
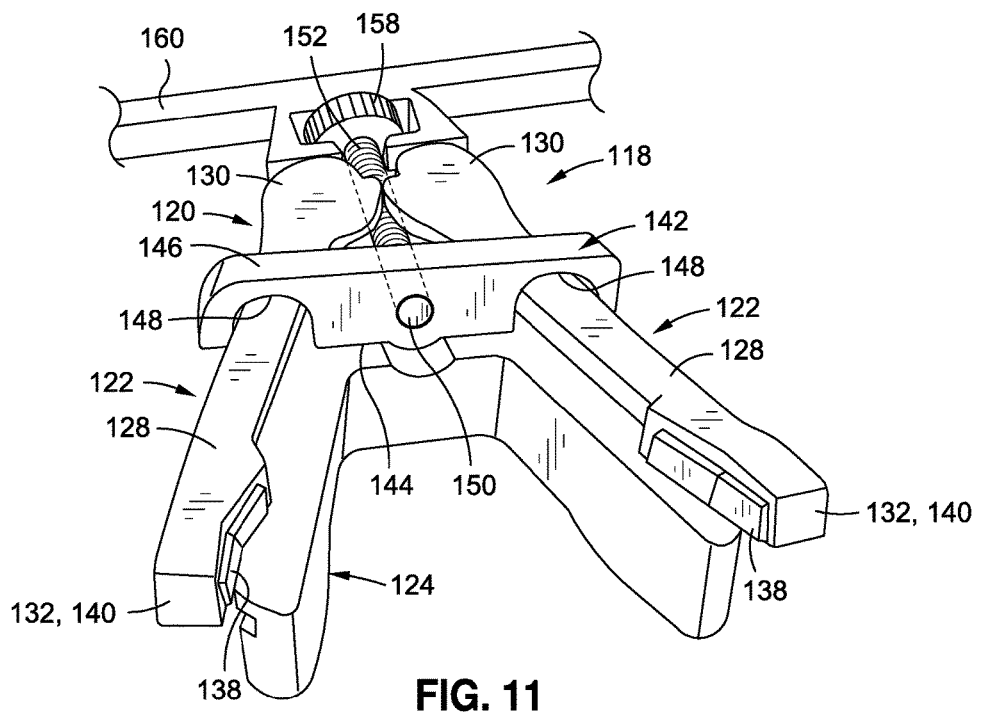
FIG. 11 is a rear lower perspective view of the third embodiment of the eyewear lens mounting device.
Figure 15:
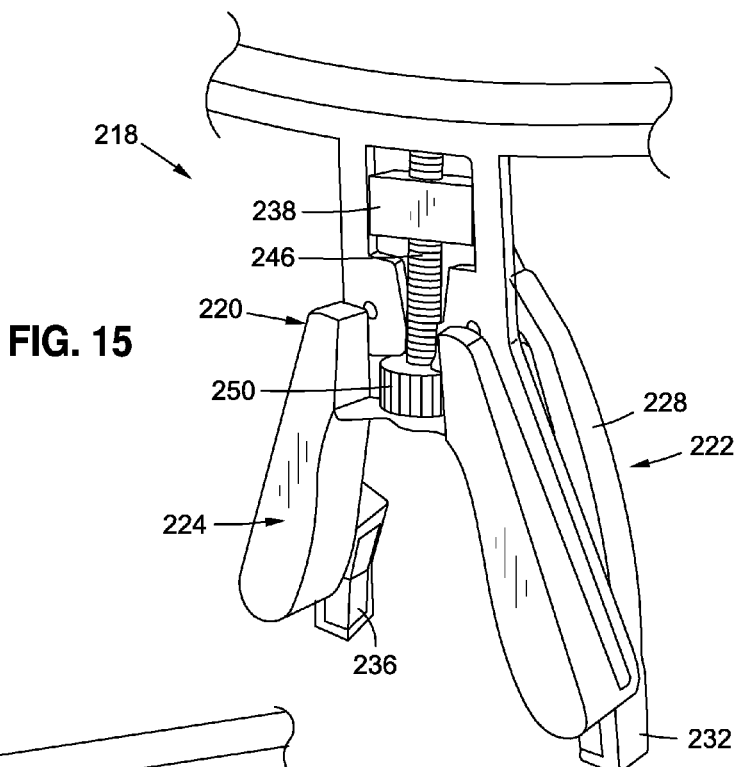
FIG. 15 is a front upper perspective view of a fourth embodiment of an eyewear lens mounting device integrated into an eyewear frame.
Figure 16:
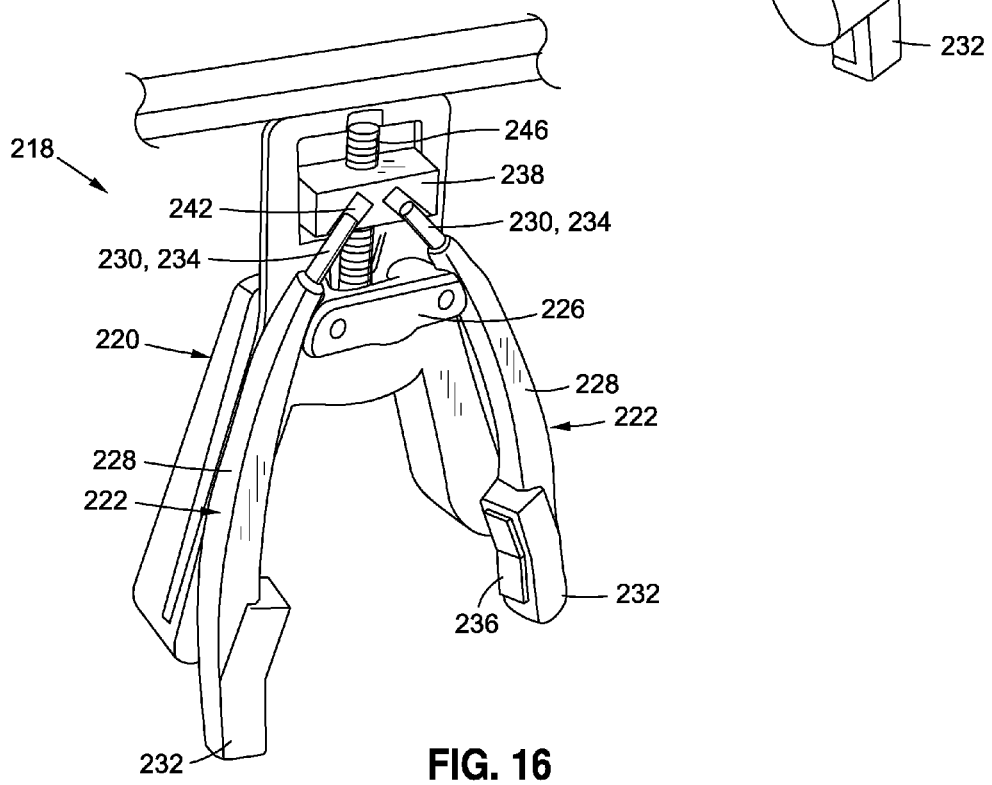
FIG. 16 is a rear upper perspective view of the fourth embodiment of the eyewear lens mounting device.
Figure 18:
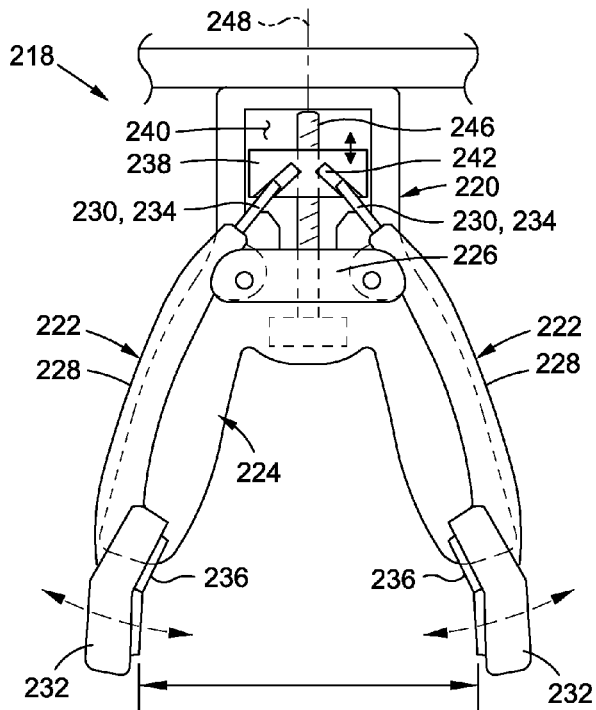
FIG. 18 is a rear view of the fourth embodiment of the eyewear lens mounting device in a narrow configuration.
Figure 17:
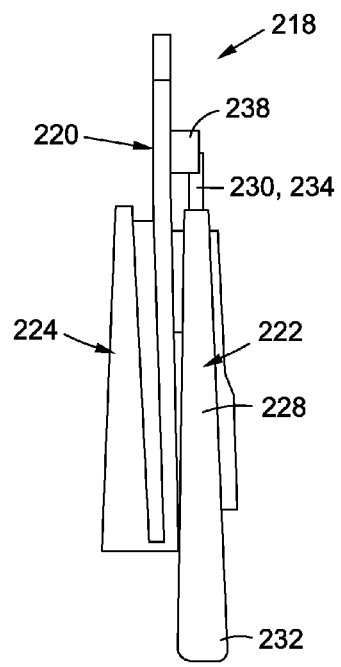
FIG. 17 is a side view of the fourth embodiment of the eyewear lens mounting device.
Figure 19:
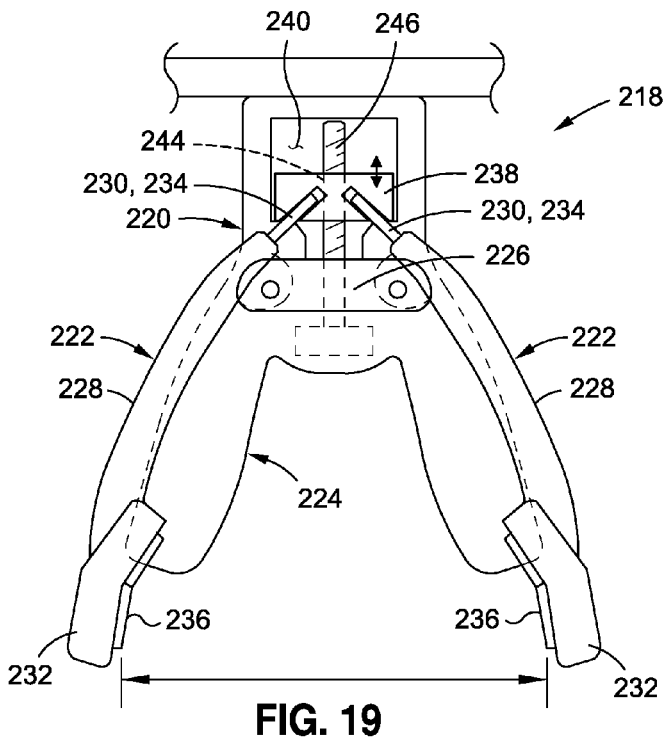
FIG. 19 is a rear view of the fourth embodiment of the eyewear lens mounting device in a wide configuration.
Figure 20:
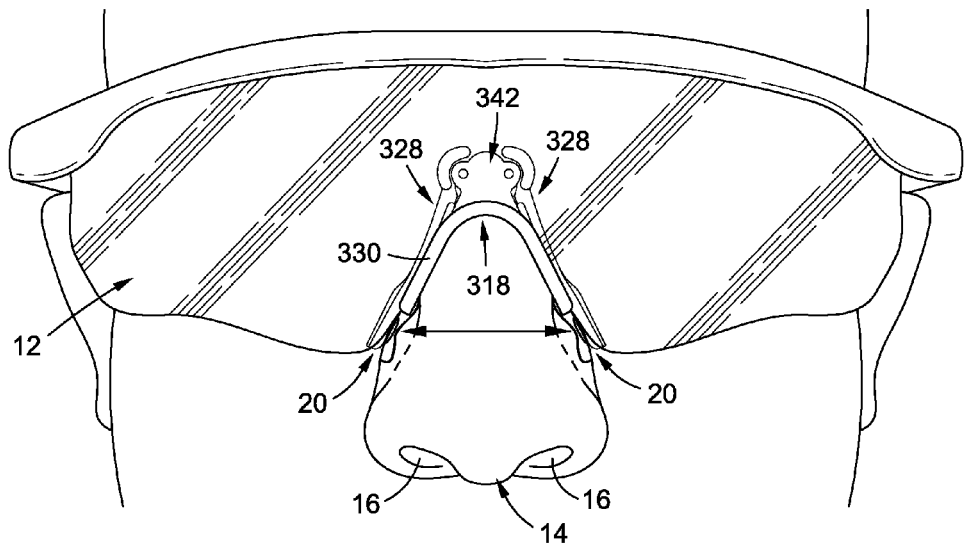
FIG. 20 is a front view of a fifth embodiment of a system including an eyewear lens mounting device and a pair of nasal appliques.
Figure 21:
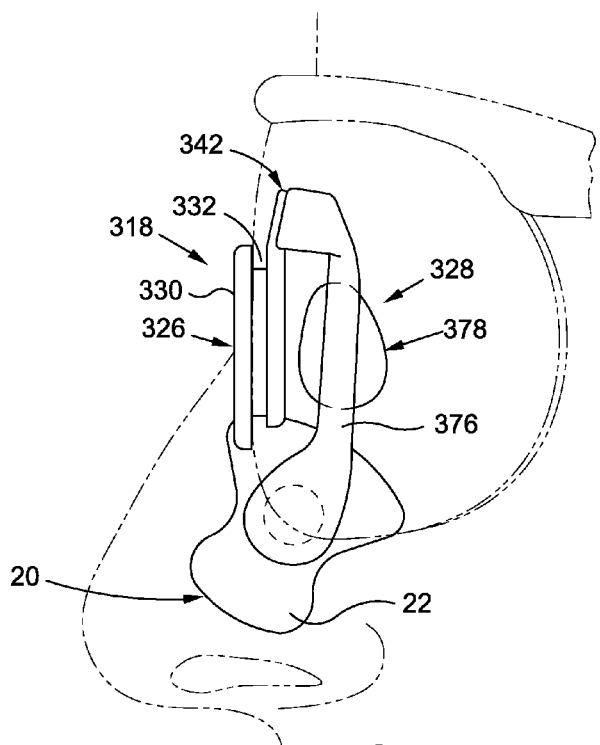
FIG. 21 is a side view of the system depicted in FIG. 20.

Referring now to FIGS. 8 and 9, there is shown another embodiment of an eyewear lens mounting device 18*a* similar to the embodiment shown in FIGS. 1-7, with the primary distinction being the inclusion of a retaining strap 80. Along these lines, the eyewear lens mounting device 18 shown in FIGS. 1-7 is particularly suited for use with eyewear having a securing mechanism, such as arms which extend around the wearer's ears or a strap which extends around the wearer's head. In this regard, without such a securing mechanism, the eyewear device 18 would pivot about the appliques 20 over the front of the user's nose 14.

The retaining strap 80 shown in FIGS. 8 and 9 is intended as a substitute for conventional securing mechanisms. In this regard, the retaining strap 80 is configured to retain the eyewear lens mounting device 18*a* on the wearer's nose 14 without arms or other similar conventional securing mechanisms. In the exemplary embodiment the retaining strap 80 extends from side segment 31*a* of the bridge member 30 to the opposing side segment 31*b* so that when the device 18*a* is worn by the wearer, the retaining strap 80 extends over the wearer's nose 14 so as to prevent the device 18*a* from pivoting over the front of the user's nose 14. In this respect, the device 18*a* is supported on the wearer's nose 14 by at least three points of contact, i.e., supported on each side of the wearer's nose 14 via the nasal appliques 20, as well as being supported by the retaining strap 80. Thus, the three points of support allows the device 18*a* to function similar to a conventional tripod.

It is understood that the mounting of the retaining strap 80 is not limited to being mounted on the bridge member 30. Rather, the retaining strap 80 may be mounted to the pivot units, directly to the lens(es), or on the eyewear frame.

Referring now to FIGS. 10-14, there is depicted another embodiment of an eyewear lens mounting device 118. The device 118 generally includes a base 120 and a pair of pivot units 122 pivotally coupled to the base 120, with the pivot units 122 being configured to interact with the nasal appliques 20 to magnetically couple the pivot units 122 to the nasal appliques 20. According to one embodiment, the base 120 is comprised of a bridge element 124 adapted to receive the eyewear lens 12 and a hinge element 126 adapted to pivotally engage with the pivot units 122. The bridge element 124 is similar to the bridge element 30 discussed above. The bridge element 124 and hinge element 126 shown in the exemplary embodiment are integral with each other, although it is understood that the bridge element 124 and hinge element 126 may be separate components which cooperate with each other.

The hinge element 126 is pivotally coupled to the pivot units 122 to enable pivotable movement of each pivot unit 122 relative to the base 120. Each pivot unit 122 includes a pivot arm 128 pivotally coupled to the hinge element 126 and including a first end portion 130 and an opposing second end portion 132. In the exemplary embodiment, the first end portion 130 of each pivot arm 128 includes a pivot boss 134 which is received with a respective hinge bore 136 formed on the hinge element 126 to pivotally couple the pivot arm 128 to the hinge element 126. The second end portion 132 of each pivot arm 128 is coupled to at least one magnet 138, and preferably a pair of magnets 138, as described above. Along these lines, the second end portion 132 of each pivot arm 128 forms a magnet holder 140 sized and configured to engage with one, and more preferably, a pair of magnets 138. The magnet holders 140 shown in FIGS. 10-14 define a slimmer form factor than the magnet holders 60 depicted in FIG. 1-7. The magnets 138 are preferably arranged in the offset, "V" shaped configuration described above.

Pivotal movement of the pivot units 122 is controlled via a guide member 142, which is adapted to translate relative to the base 120. The guide member 142 is also coupled to the pivot units 122 in a manner which transforms the translational movement of the guide member 142 into pivotal movement of the pivot units 122. The guide member 142 includes a first face 144 facing toward the base 120 and an opposing second face 146 facing away from the base 120. The guide member 142 also includes a pair of grooves 148 extending into the guide member 142 from the first face 144 toward the second face 146. Each groove 148 is adapted to have one of the pivot arms 128 extend therethrough.

An adjustment bore 150 is formed within the guide member 142 and is adapted to receive an adjustment shaft 152, which rotates about a rotation axis 154. The guide member 142 and adjustment shaft 152 are cooperatively configured to transform rotational movement of the adjustment shaft 152 into axial movement of the guide member 142. The adjustment bore 150 includes internal threads that engage with the external threads on the adjustment shaft 152 so that as the adjustment shaft 152 rotates in a first rotational direction, the guide member 142 moves relative to the base 120 along the adjustment shaft 152 (and the rotation axis 154) in a first axial direction, and as the adjustment shaft 152 rotates in an opposing second rotational direction, the guide member 142 moves along the adjustment shaft 152 in an opposing second axial direction. Thus, by rotating the adjustment shaft 152, the guide member 142 can move relative to the base 120.

A portion of each pivot arm 128 is fixed about a respective pivot axis 156 relative to the hinge element 126 and base 120 by virtue of the pivot bosses 134 being received within corresponding hinge bores 136. In this regard, the pivot bosses 134 may pivot about a respective pivot axis 156, but the distance between the pivot bosses 134 remains fixed. In contrast, the distance between the second end portions 132 of the pivot arms 128 may be varied as a result of the pivoting motion of the pivot arms 128.

The pivoting motion of the pivot arms 128 is controlled by the guide member 142. In particular, as the guide member 142 translates relative to the base 120, the guide member 142 slides along the pivot arms 128, which causes the pivot arms 128 to pivot relative to the hinge element 126, and to move relative to each other. When viewed from the perspective shown in FIGS. 13 and 14, as the guide member 142 moves down, the second end portions 132 of the pivot arms 128 are moved toward each other to assume a narrow configuration (see FIG. 13). In contrast, as the guide member 142 moves up, the second end portions 132 of the pivot arms 128 are moved away from each other such that the pivot arms 128 assume a wide configuration (see FIG. 14).

Movement of the guide member 142 is associated with rotation of the adjustment shaft 152. A manually-operated adjustment knob 158 is coupled to the adjustment shaft 152 to rotate the adjustment shaft 152. A user may rotate the adjustment knob 158 in a first rotational direction to effectuate rotation of the adjustment shaft 152 in the first rotational direction. Likewise, the user may rotate the adjustment knob 158 is a second rotational direction to effectuate rotation of the adjustment shaft 152 in the second rotational direction. The adjustment knob 158 is located near the top of the device 118, adjacent the frame 160 of the eyewear. In this respect, a slot may be cut through the lens to enable manual access to the adjustment knob 158 while the wearer is wearing the device 118. In this regard, the wearer may quickly and easily adjust the magnitude of the dilating force during use/on-the-fly by simply rotating the adjustment knob 158.

As shown in FIGS. 10-14, the device 118 is integrally formed with the eyewear frame 160. In this respect, the device 118 may be molded with the forward frame element which may extend along an upper edge of the eyewear lens 12.

Referring now to FIGS. 15-19, there is shown another variation of an eyewear lens mounting device 218. The device 218 generally includes a base 220 and a pair of pivot units 222 pivotally coupled to the base 220, with the pivot units 222 being configured to interact with the nasal appliques 20 to magnetically couple the pivot units 222 to the nasal appliques 20. According to one embodiment, the base 220 includes a bridge element 224 adapted to receive the eyewear lens 12. The bridge element 224 is similar to the bridge element discussed above.

The base 220 further includes a fulcrum element 226 (e.g., hinge element) coupled to the bridge element 224, with the fulcrum element 226 providing a structure upon which the pivot units 222 pivot. Each pivot unit 222 includes a pivot arm 228 having a first end portion 230 and an opposing second end portion 232. In the exemplary embodiment, the first end portion 230 of each pivot arm includes an attachment stem 234. The second end portion 232 of each pivot arm is similar to the second end portion 132 described above in relation to FIGS. 10-14, and is coupled to at least one magnet 236, and preferably a pair of magnets 236.

Pivotal movement of the pivot units 222 is controlled via a guide member 238, which translates relative to the base 220 in an opening 240. The guide member 238 and pivot units 222 are configured such that the translational movement of the guide member 238 is transferred into pivotal movement of the pivot units 222. The guide member 238 includes a pair of channels 242 extending into the guide member 238, with the channels 242 being specifically sized and configured to receive a respective attachment stem 234 to connect the pivot units 222 to the guide member 238. An adjustment bore 244 is formed within the guide member 238 and is adapted to receive an adjustment shaft 246, which rotates about a rotation axis 248. The guide member 238 and adjustment shaft 246 are cooperatively configured to transform rotational movement of the adjustment shaft 246 into axial movement of the guide member 238. The adjustment bore 244 includes internal threads that engage with the external threads on the adjustment shaft 246 so that as the adjustment shaft 246 rotates in a first rotational direction, the guide member 238 moves relative to the base 220 along the adjustment shaft 246 (and the rotation axis 248) in a first axial direction, and as the adjustment shaft 246 rotates in an opposing second rotational direction, the guide member 238 moves along the adjustment shaft 246 in an opposing second axial direction. Thus, by rotating the adjustment shaft 246, the guide member 238 can move relative to the base 220.

The pivoting motion of the pivot arms 222 is controlled by the guide member 238 and the fulcrum element 226. In particular, as the guide member 238 translates, the first end portions 230 of the pivot arms 228 are moved closer or farther away from the fulcrum element 226, which results in the pivotal movement of the pivot arms 222. When viewed from the perspective shown in FIGS. 18 and 19, as the guide member 238 moves up, the second end portions 232 of the pivot arms 228 are moved toward each other to assume a narrow configuration (see FIG. 18). In contrast, as the guide member 238 moves down, the second end portions 232 of the pivot arms 228 are moved away from each other such that the pivot arms 228 assume a wide configuration (see FIG. 19).

A manually-operated adjustment knob 250 is coupled to the adjustment shaft 246 to rotate the adjustment shaft 246. A user may rotate the adjustment knob 250 in a first rotational direction to effectuate rotation of the adjustment shaft 246 in the first rotational direction. Likewise, the user may rotate the adjustment knob 250 in a second rotational direction to effectuate rotation of the adjustment shaft 246 in the second rotational direction. The adjustment knob 250 is located near the bottom of the adjustment shaft 246, adjacent the bridge member 224. In this respect, the adjustment knob 250 may be located beneath the lens 12, or alternatively, a slot may be cut through the lens 12 to enable manual access to the adjustment knob 250 while the wearer is using the device 218. In this regard, the wearer may quickly and easily adjust the magnitude of the dilating force during use/on-the-fly by simply rotating the adjustment knob 250.

Referring now to FIGS. 20-25, there is depicted another embodiment of an eyewear lens mounting device 318 including a base 326 and a pair of pivot units 328 pivotally coupled to the base 320. In the exemplary embodiment the hinge element 342 is integrally formed with the bridge element 330, and the pivot units 328 are disposed on opposite sides of a central axis 345. Each pivot unit 328 is adapted to magnetically interact with one or more nasal appliques 20 to impart a dilating force on the user's nose 14.

The base 326 includes a bridge element 330 and a hinge element 342. The hinge element 42 is coupled to the bridge element 330 and includes a first hinge portion 344 pivotally coupled to the first pivot unit 328a and a second hinge portion 346 pivotally coupled to the second pivot unit 328b. Furthermore, the bridge element 330 may include a pair of terminal ends 338 respectively formed on the bridge element arms, wherein the terminal ends 338 are configured to abut respective protrusions 41 formed on a corresponding bridge region of the eyewear lens 12 for connecting the eyewear lens 12 to the bridge element 330. In particular, the protrusions 41 may extend around the terminal ends 338 of the bridge element 330 to prevent the eyewear lens 12 from being inadvertently disconnected from the bridge element 330. Of course, other mechanisms for attaching the eyewear lens 12 to the bridge element 330 may also be used without departing from the spirit and scope of the present disclosure, such as other snap-fit arrangements. It is also contemplated that in one particular embodiment, the bridge element 330 is overmolded onto the eyewear lens 12 to create a more permanent connection therebetween.

Figure 22:
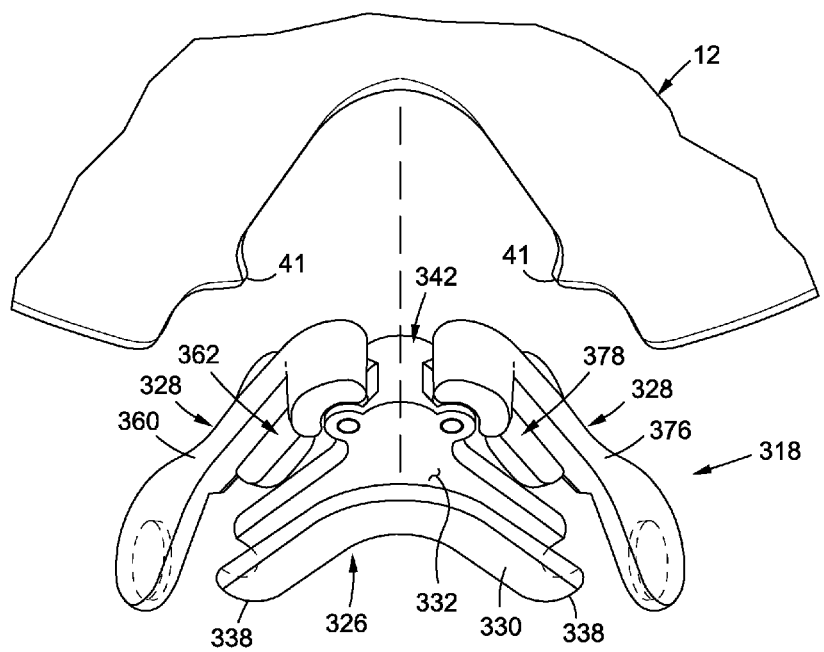
FIG. 22 is an upper perspective view of the eyewear lens mounting device of FIGS. 20-21 detached from an eyewear lens.
Figure 23:
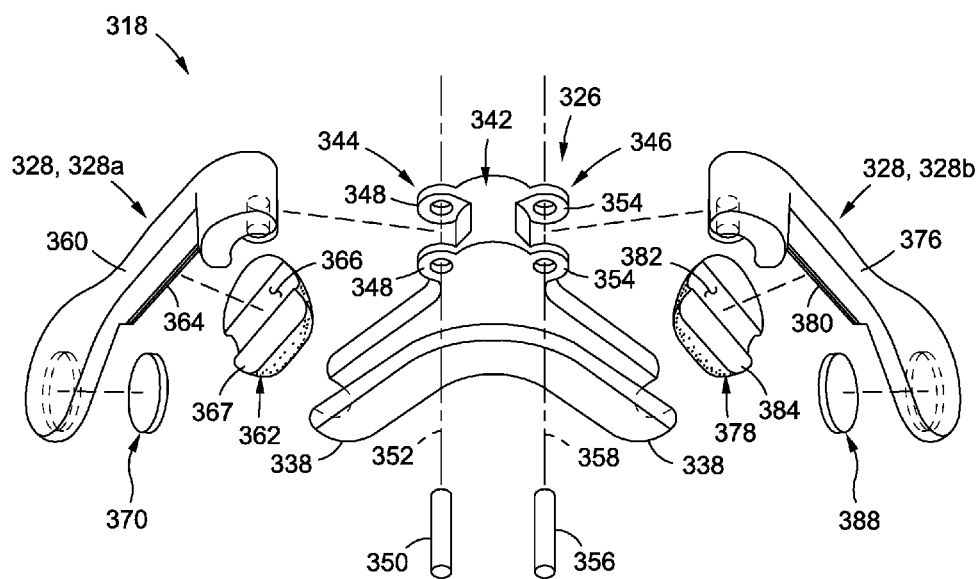
FIG. 23 is an upper perspective exploded view of the eyewear lens mounting device shown in FIGS. 20-22.
Figure 24:
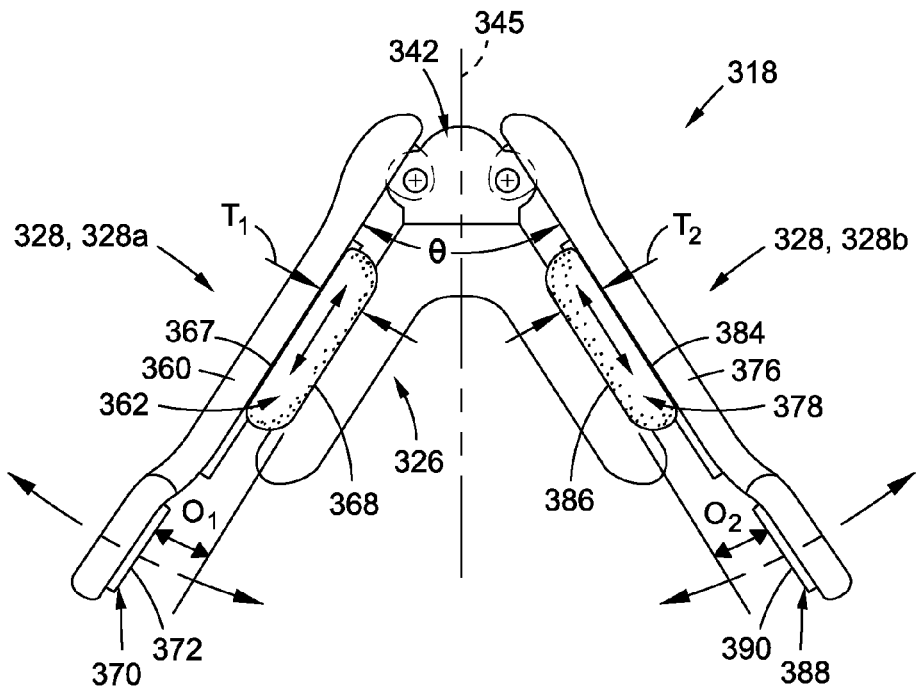
FIG. 24 is a front view of the eyewear lens mounting device of FIGS. 20-23 shown in a wide configuration.
Figure 25:
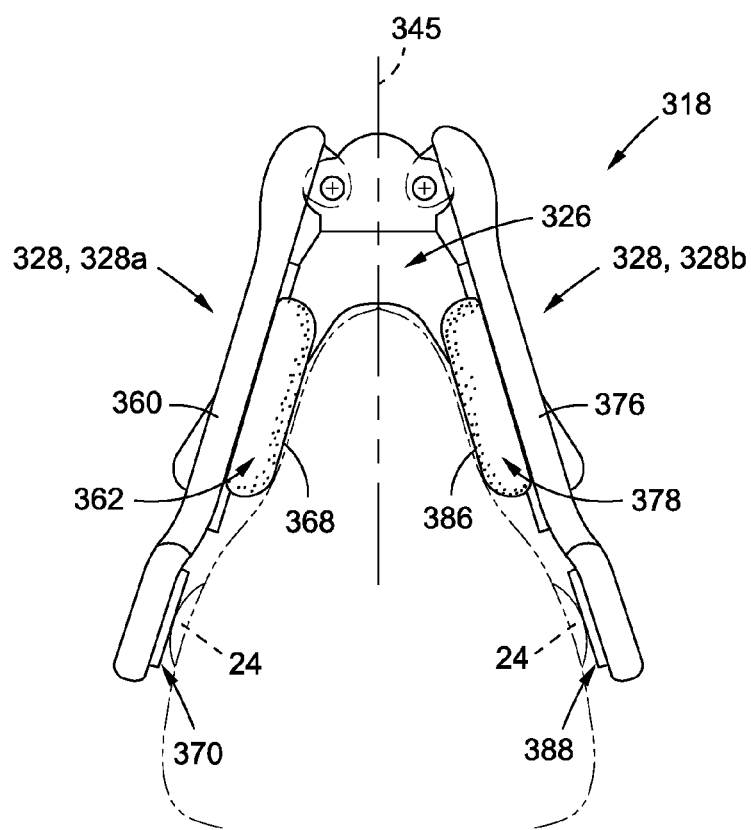
FIG. 25 is a front view of the eyewear lens mounting device of FIGS. 20-23 shown in a narrow configuration relative to the wide configuration depicted in FIG. 24.

Referring now specifically to FIG. 22, the first hinge portion 344 includes a pair of tabs 348 spaced apart and defining a pair of co-axially aligned openings, with the spacing between the tabs 348 being adapted to receive a portion of the first pivot unit 328a. A first pivot pin 350 is advanced through the tabs 348 and the first pivot unit 328a to pivotally couple the first pivot unit 328a to the first hinge portion 344, such that the first pivot unit 328a is pivotal relative to the base 326 about a first pivot axis 352. The second hinge portion 346 is configured similar to the first hinge portion 344 and includes a pair of tabs 354 spaced apart and defining a pair of co-axially aligned openings, with the spacing between the tabs 354 being adapted to receive a portion of the second pivot unit 328b. A second pivot pin 356 is advanced through the tabs 354 and the second pivot unit 328b to pivotally couple the second pivot unit 328b to the second hinge portion 346, such that the second pivot unit 328b is pivotal relative to the base 326 about a second pivot axis 358.

According to one embodiment, the first pivot unit 328a includes a first pivot arm 360 and a first pad 362 coupled to the first pivot arm 360, with the first pivot arm 360 being pivotally coupled to the base 326. The first pad 362 is adapted to rest on the user's nose, and serve as a fulcrum about which the first pivot arm 360 acts on the applique 20. The first pad 362 is translatable along the first pivot arm 360. According to one embodiment, the first pivot arm 360 may include a ridge or spine 364, and the first pad 362 includes a corresponding groove 366 which receives the spine 364 to translatably couple the first pad 362 to the first pivot arm 360. The first pad 362 includes a first surface 367 facing toward the first pivot arm 360 and a second surface 368 facing away from the first pivot arm 360 and defining an engagement face which engages with the user's nose 14 during use of the lens mounting device 18. The first pad 362 defines a first pad thickness, $T_1$, as the distance between the first surface 367 and the second surface 368. The first pivot unit 328a further includes a first magnet 370 coupled to a distal end portion of the first pivot arm 360, with the first magnet 370 defining a first magnet inward surface 372 facing toward the central axis 345. The second surface 368 of the first pad 362 and the first magnet inward surface 372 are offset from each other by an offset distance, $O_1$, the importance of which will be described in more detail below.

The second pivot unit 328b is configured similar to the first pivot unit 328a and includes a second pivot arm 376 and a second pad 378 coupled to the second pivot arm 376, with the second pivot arm 376 being pivotally coupled to the base 326. The second pad 378 is adapted to rest on the user's nose, and serve as a fulcrum about which the second pivot arm 376 acts on the applique 20. The second pad 378 is translatable along the first pivot arm 376. According to one embodiment, the second pivot arm 376 includes a ridge or spine 380, and the second pad 378 includes a corresponding groove 382 which receives the spine 380 to translatably couple the second pad 378 to the second pivot arm 376. The second pad 378 includes a first surface 384 facing toward the second pivot arm 376 and a second surface 386 facing away from the second pivot arm 376 and defining an engagement face which engages with the user's nose 14 during use of the lens mounting device 18. The second pad 378 defines a second pad thickness, $T_2$, as the distance between the first surface 384 and the second surface 386. The second pivot unit 328b further includes a second magnet 388 coupled to a distal end portion of the second pivot arm 376, with the second magnet 388 defining a second magnet inward surface 390 facing toward the central axis 345. The second surface 386 of the second pad 378 and the second magnet inward surface 390 are offset from each other by an offset distance, $O_2$.

In the embodiment depicted in FIGS. 20-25, the magnets 370, 388 are located within respective cavities formed in the pivot arms 360, 376. In particular, the cavities extend into the respective pivot arms 360, 376 from an inner surface thereof, e.g., a surface which faces the nose 14 when the device 18 is worn on the nose 14. In the exemplary embodiment, the magnets 370, 388 are circular disks, and thus, the distal end portions of the pivot arms 360, 376 include an enlarged, rounded end to accommodate the disk-shaped magnets 370, 388. It is also contemplated that multiple magnets may be coupled to each pivot arm 360, 376 and arranged in an angled configuration, as discussed above.

The first pivot arm 360 and the second pivot arm 376 are positioned on opposite sides of the central axis 345 and define a nose adjustment angle, $\Theta$, therebetween, with the nose adjustment angle $\Theta$ being generally conformable to the user's nose 14. In this respect, the size of the nose adjustment angle $\Theta$ may be adjusted so as to correspond to the size of the user's nose 14.

According to one embodiment, the strength of the dilating force imparted on the user's nose is directly related to the magnitude of the offsets, $O_1$ and $O_2$, which are defined by the thicknesses $T_1$ and $T_2$ of the pads 362, 378. In particular, as the magnitude of the offsets $O_1$ and $O_2$ increases, the magnitude of the respective dilating forces (e.g., the dilating forces imparted on the sides of the nose) also increases. Conversely, as the magnitude of the offsets $O_1$ and $O_2$ decreases, the magnitude of the respective dilating forces also decreases. Therefore, according to one embodiment, the magnitude of the dilating forces may be selected by choosing pads 362, 378 having thicknesses $T_1$ and $T_2$ which correspond to the desired dilating force. In this respect, it is contemplated that the pads 362, 378 are removable from the corresponding pivot arms 360, 376 to allow the user to vary the magnitude of the dilating force by swapping out pads having an undesirable thickness for pads having a more desirable thickness.

Use of the system includes placing one or more of the nasal appliques 20 adjacent the lateral regions of the user's nose 14, and preparing the lens 12 and lens mounting device 318 for use. In particular, if the lens mounting device 318 is not molded onto the lens 12, the user may select which lens 12 is to be used and placed in the lens receiving channel 332. The ability to select the lens 12 may allow for customization of the system 10 based on the environmental conditions. For instance, if the device 318 is going to be used in a bright, sunny environment, the user may select a tinted lens 12, whereas if the device 318 is going to be used in a darker environment, the user may select a clear lens 12. Preparation of the lens mounting device 318 also includes ensuring the pads 362, 378 having a desired thickness associated with the preferred dilating force are placed on the pivot arms 360, 376.

Once the appliques 20 are placed on the nose 14 and the lens is coupled to the lens mounting device 318, the lens mounting device 318 is placed on the user's nose, with the lens 12 being positioned in front of the user's eyes. As the lens mounting device 318 is moved closer to the nose 14, the metallic elements 24 are drawn outwardly toward the magnets 370, 388. Furthermore, the magnetic attraction between the metallic elements 24 and the magnets 370, 388 causes the pivot arms 360, 376 to pivot relative to the base 326 and conform to the size of the user's nose 14. When the lens retaining device 318 is finally positioned on the user's nose 14, the magnetic attraction between the metallic elements 24 and the magnets 370, 388 imparts a dilating force on the user's nose 14 to open the nasal passageway 16. During use of the system, the user can self-adjust the location of the lens 12 by moving the lens 12 up or down the user's nose 14, which may also vary the dilating force imparted on the user's nose 14.

When the user wants to remove the lens 12 from the user's nose 14, the user may simply slide the lens mounting device 18 forward over the tip of the user's nose 14, which causes the magnets 370, 388 to slide over the surface of the metallic elements 24 and then move away from the metallic elements 24 to effectively eliminate the magnetic attraction therebetween and terminate the dilating force.

Figure 26:
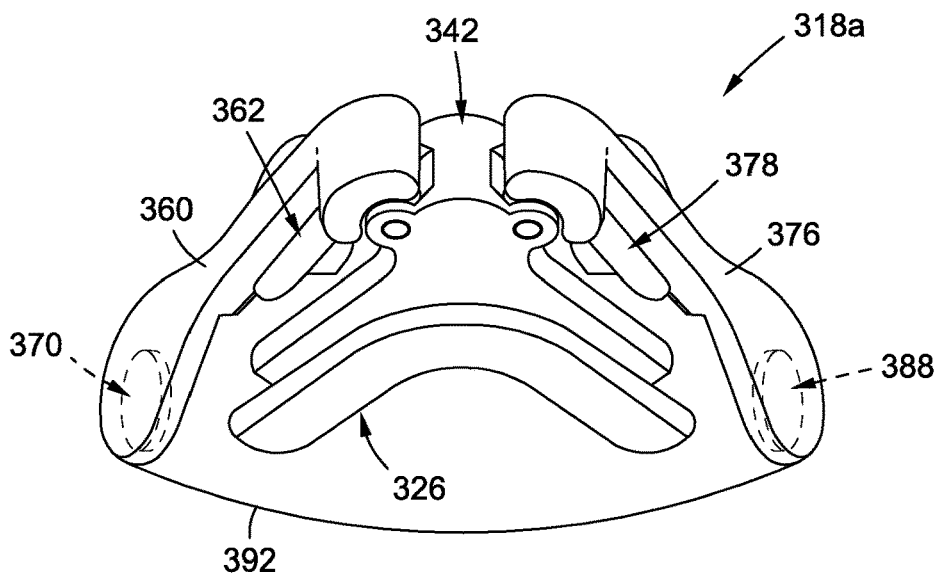
FIG. 26 is an upper perspective view of a sixth embodiment of an eyewear lens mounting device including a nasal retaining member.
Figure 27:
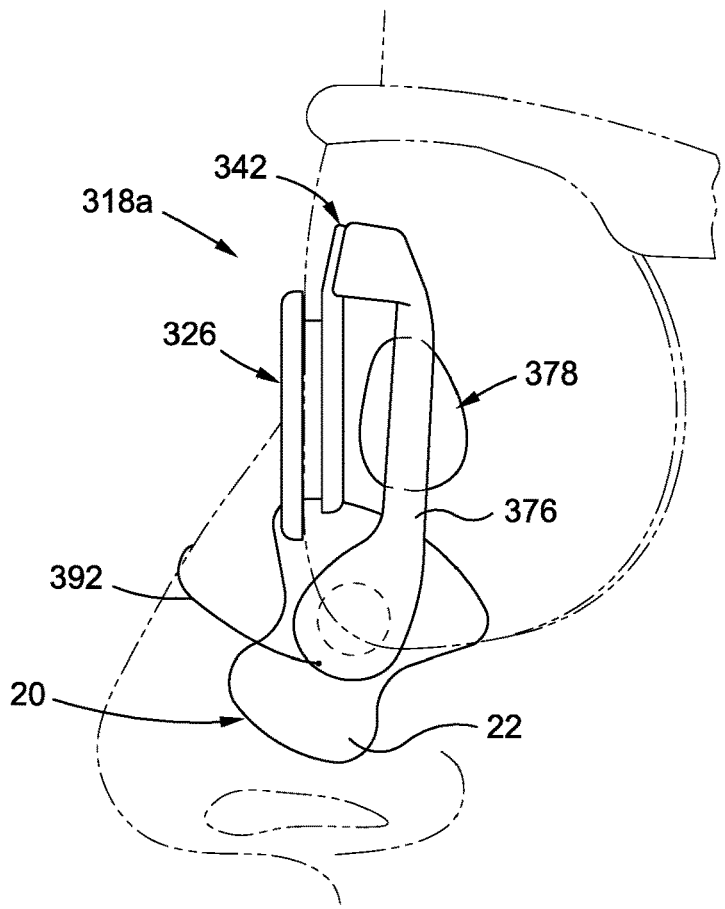
FIG. 27 is a side view of a system including the eyewear lens mounting device depicted in FIG. 28.
Figure 28:
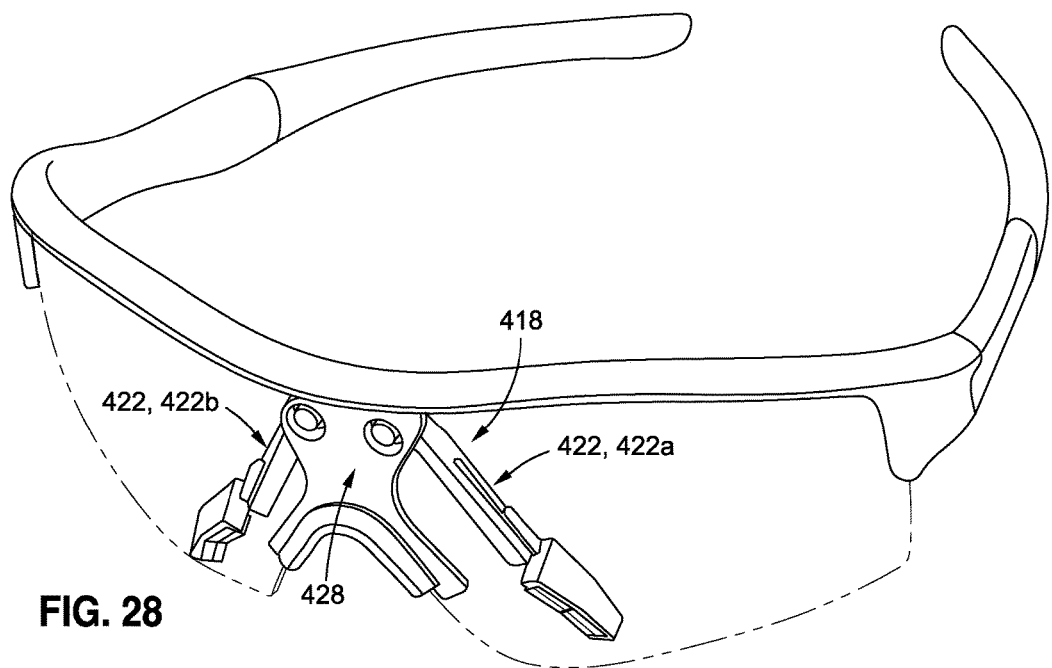
FIG. 28 is a front upper perspective view of a seventh embodiment of an eyewear lens mounting device integrated into an eyewear frame.
Figure 29:
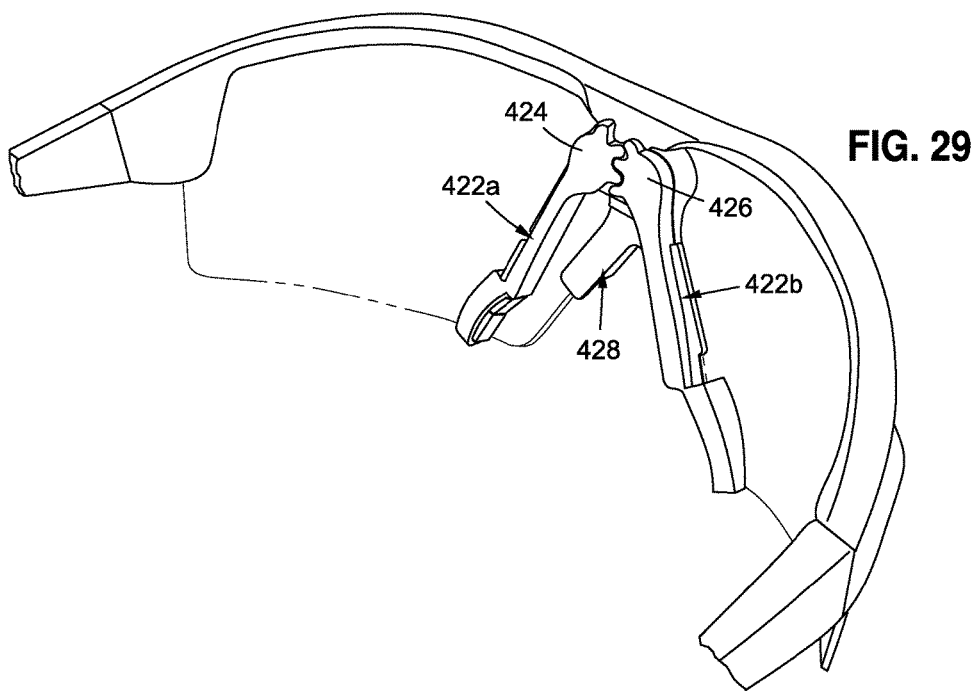
FIG. 29 is a rear upper perspective view of the seventh embodiment of the eyewear lens mounting device.
Figure 30:
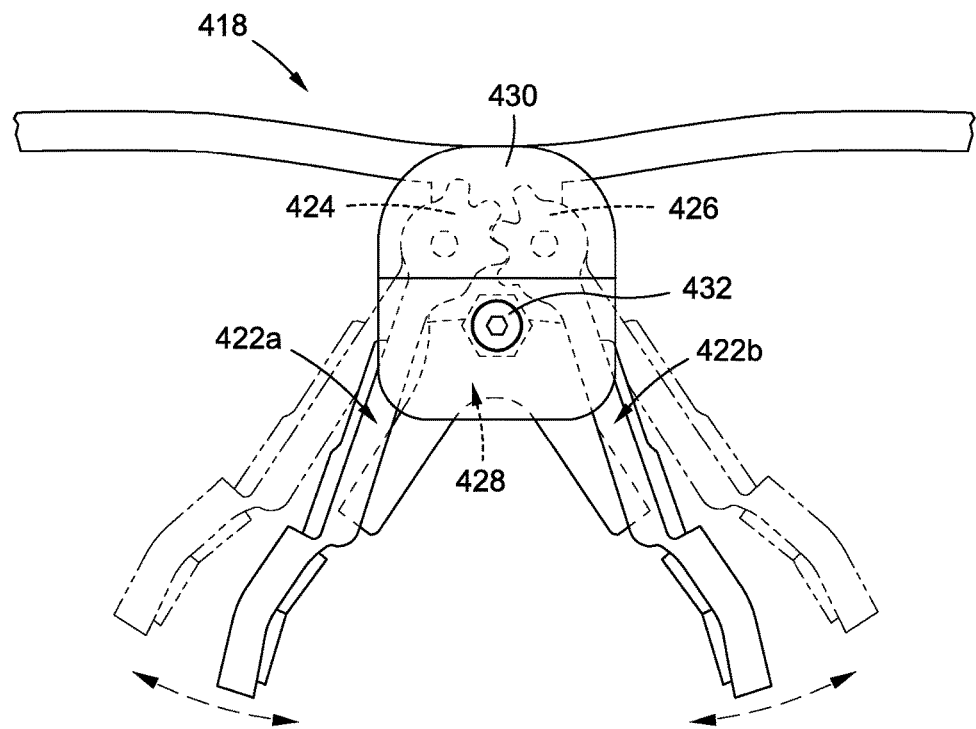
FIG. 30 is a front view of the seventh embodiment of the eyewear lens mounting device.
Figure 31:
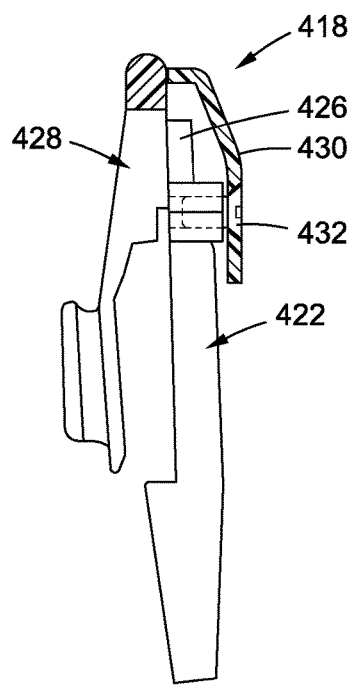
FIG. 31 is a side view of the seventh embodiment of the eyewear lens mounting device.

Referring now to FIGS. 26 and 27, there is depicted another embodiment of the lens mounting device 318a, with the primary difference being the inclusion of a retaining member 392 coupled to and extending between the first pivot arm 360 and the second pivot arm 376 and adapted to engage with the user's nose 14 to retain the lens mounting device 318a on the user's nose 14, particular when the lens mounting device 318a is used with lenses formed without arms which extend behind the user's ears. The retaining member 392 may be an elastic band, strap, or piece of tubing which extends between the pivot arms 360, 376. The retaining member 392 is pliable or stretchable to enable the pivot arms 360, 376 to pivot relative to the base 326, as described in more detail above. Alternatively, a retaining member 392 that is not stretchable may be used, such as a band which could be lengthened or shortened at one or both ends to accommodate different noses.

Referring now to FIGS. 28-31, there is depicted another embodiment of the lens mounting device 418 which includes a pair of pivot units 422 similar to the pivot units discussed above in relation to the previous embodiments. The primary distinction is that that pivot units 422 shown in FIGS. 28-31 are geared together, such that pivotal movement of one pivot unit 422 causes pivotal movement of the other pivot unit 422, whereas the previous embodiments discussed above include pivot units that are capable of pivoting independent of each other.

Each pivot unit 422 is pivotally coupled to a base 428, with a first pivot unit 422a having a first gear portion 424 and a second pivot unit 422b having a second gear portion 426. The first gear portion 424 includes a series of gear teeth which cooperatively engage with a corresponding series of gear teeth on the second gear portion 426. The first and second gear portions 424, 426 may be covered by a cap 430, which may be secured to the base 428 by a screw 432 or other attachment mechanisms known in the art. The cap 430 provides at least partial coverage over the gear portions 424, 426 to protect against debris from interfering with the operability of the gear portions 424, 426. The cap 430 may also further secure the pivot units 422a,b to the base 428.

Although the foregoing describes the pivot arms as being coupled to a base adapted to engage one or more eyewear lenses, it is contemplated that other embodiments of the device may include pivot arms that are directly connected to the lenses, and thus, do not require a base as shown. In particular, the lens(es) may include one or more apertures drilled therein, and the pivot arms may be mounted to the lenses using the apertures. In this regard, mounting hardware may be used to effectuate such mounting.

Figure 32:
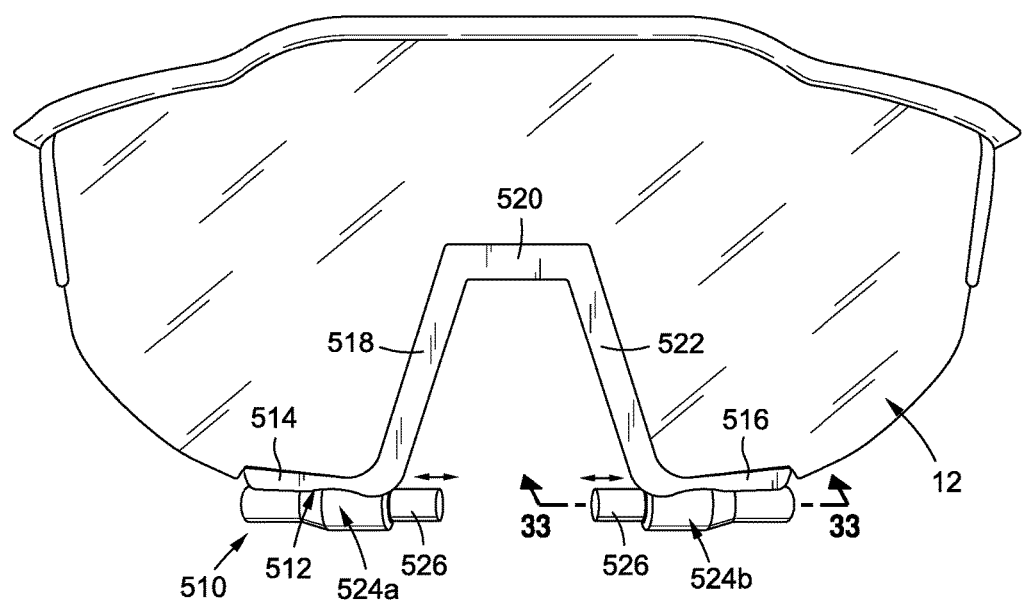
FIG. 32 is a front view of an eighth embodiment of an eyewear lens mounting device.
Figure 33:
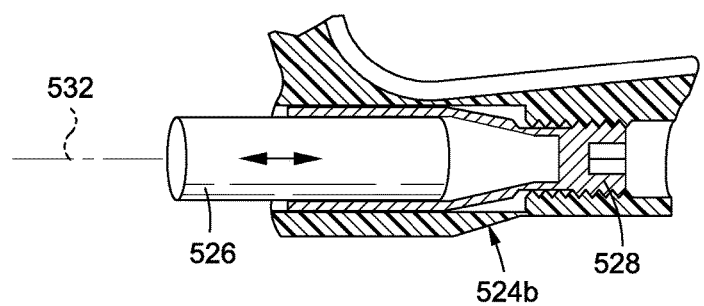
FIG. 33 is a partial cross sectional view of the eighth embodiment of the eyewear lens mounting device.

Referring now to FIGS. 32 and 33, there is depicted another embodiment of a device 510 mountable on a wearer's lens 12 and adapted to magnetically interact with one or more appliques 20 worn by the wearer. The device 510 includes a main body 512 attachable to the lens 12, wherein the main body 512 includes a channel adapted to receive a peripheral portion of the lens 12. According to one embodiment, the main body 512 includes a first lower lens segment 514, and a second lower lens segment 516. In the exemplary embodiment, the first and second lower lens segments 514, 516 are coupled to each other via a first side segment 518, an apex segment 520, and a second side segment 522. However, it is also contemplated that the first and second lower lens segments 514, 516 may be separate components which attach to separate lenses or separate regions of a common lens. A first magnet housing 524a is coupled to the first lower lens segment 514 and a second magnet housing 524b is coupled to the second lower lens segment 516. Each magnet housing 524a,b includes a recess or opening adapted to receive a magnet 526, with each magnet 526 being operatively coupled to a magnet adjuster 528. The magnets 526 are adapted to magnetically interact with the nasal appliques 20 when the lens is worn by the wearer. In the exemplary embodiment, the magnet adjuster 528 is capable of adjusting the corresponding magnet 526 along an adjustment axis 532. The magnet adjuster 528 may be a set screw operatively coupled to the magnet 526. The adjustment axes 532 are preferably co-axially aligned with each other, although the present disclosure is not limited thereto, i.e., the adjustment axes may be angularly offset from one another. The magnets 526 are independently movable along their respective adjustment axis to change the position of the magnet 526 relative to the respective magnet housings 524a,b which in turn adjusts the dilating force on the wearer's nose. In particular, as the magnets 526 are moved away from the wearer's nose, the dilating force increases because the appliques 20 are required to move a farther distance to physically interact with the magnets 526. Conversely, as the magnets 526 are moved towards the wearer's nose, the dilating force decreases, as the appliques 20 do not need to move as far to physically interact with the magnets.

It is contemplated that any of the foregoing embodiments of the device may be configured as a component which is separate from the eyewear frame, or alternatively, any one of the embodiments may be integrally formed with the eyewear frame, such that the device and the eyewear frame operate as a single unit. In this regard, some embodiments of the device may at least partially rely on the eyewear lens(es) for support, while other embodiments may be adapted such that they do not require structural support from the eyewear lens(es). Furthermore, any one of the foregoing embodiments may be adapted for use with a single lens, or a plurality of lenses, such as two lenses.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A device for coupling at least one eyewear lens to at least one nasal applique attachable to a user's nose which results in dilation of a nasal passageway, the device comprising:
    a base engageable with the at least one eyewear lens;
    an adjustment shaft coupled to the base and extending longitudinally along a rotation axis, the adjustment shaft being rotatable relative to the base about the rotation axis;
    a first pivot unit coupled to the base and pivotable relative to the base about a first pivot axis in response to rotation of the adjustment shaft about the rotation axis; and
    a second pivot unit coupled to the base and pivotable relative to the base about a second pivot axis in response to rotation of the adjustment shaft about the rotation axis;
    the first pivot unit and the second pivot unit being interactable with at least one nasal applique to magnetically couple the first pivot unit and the second pivot unit to the at least one nasal applique, the magnetic coupling between the first pivot unit and the second pivot unit and the at least one nasal applique imparting a dilating force on the user's nose to dilate the nasal passageway when the at least one nasal applique is attached to the user's nose.

2. The device recited in claim 1, further comprising a guide coupled to the adjustment shaft, the first pivot unit and the second pivot unit, the guide being moveable relative to the base, movement of the guide relative to the base causing pivotal movement of the first pivot unit and the second pivot unit relative to the base.

3. The device recited in claim 2, wherein the guide includes a pair of grooves formed therein, the first and second pivot units being received within respective ones of the pair of grooves.

4. The device recited in claim 2, wherein the guide includes a camming surface which interfaces with the first pivot unit and the second pivot unit, the camming surface transforming translational movement of the guide into pivotal movement of the first pivot unit and the second pivot unit.

5. The device recited in claim 2, wherein the guide is translatable along the adjustment shaft.

6. The device recited in claim 5, wherein the guide and adjustment shaft are sized and structured such that the guide is translatable along the adjustment shaft in response to rotation of the adjustment shaft about the rotation axis.

7. The device recited in claim 6, further comprising an adjustment knob coupled to the adjustment shaft and adapted to enable manually controlled rotation of the adjustment shaft about the rotation axis.

8. The device recited in claim 1, wherein the first pivot unit includes a first gear portion and the second pivot unit includes a second gear portion cooperatively engaged with the first gear portion to facilitate geared pivotal motion of the first pivot unit relative to the second pivot unit.

9. The device recited in claim 1, wherein:
    the first pivot unit includes a first pivot arm and a first pad coupled to the first pivot arm, the first pivot arm being pivotally coupled to the base;

the second pivot unit includes a second pivot arm and a second pad coupled to the second pivot arm, the second pivot arm being pivotally coupled to the base.

10. The device recited in claim 9, wherein the first pad is translatable along the first pivot arm and the second pad is translatable along the second pivot arm.

11. The device recited in claim 1, wherein:
the first pivot unit includes a first pivot arm and at least one magnet coupled to the first pivot arm;
the second pivot unit includes a second pivot arm and at least one magnet coupled to the second pivot arm.

12. The device recited in claim 1, wherein:
the first pivot unit includes a first pivot arm and a first pair of magnets coupled to the first pivot arm, the first pair of magnets being arranged in an angularly offset configuration;
the second pivot unit includes a second pivot arm and a second pair of magnets coupled to the second pivot arm, the second pair of magnets being arranged in an angularly offset configuration.

13. The device recited in claim 1, further comprising a retainer coupled to the base and adapted to engage with the user's nose to retain the device on the user's nose.

14. A system for attaching at least one eyewear lens to a user and dilating the user's nose, the system comprising:
at least one nasal applique including a base layer and a metallic element coupled to the base layer, the base layer attachable to the user's nose; and
an eyewear securing device operatively connectable to the at least one nasal applique, the eyewear securing device comprising:
a base engageable with the at least one eyewear lens;
a first pivot unit coupled to the base and pivotable relative to the base about a first pivot axis;
a second pivot unit coupled to the base and pivotable relative to the base about a second pivot axis; and
a guide coupled to the first pivot unit and the second pivot unit, the guide being moveable relative to the base, movement of the guide relative to the base causing pivotal movement of the first pivot unit and the second pivot unit relative to the base;
the first pivot unit and the second pivot unit being interactable with the at least one nasal applique to magnetically couple the first pivot unit and the second pivot unit to the at least one nasal applique, the magnetic coupling between the first pivot unit and the second pivot unit and the at least one nasal applique imparting a dilating force on the user's nose to dilate the nasal passageway when the at least one nasal applique is attached to the user's nose.

15. The device recited in claim 14, wherein the guide includes a pair of grooves formed therein, the first and second pivot units being received within respective ones of the pair of grooves.

16. The device recited in claim 14, wherein the guide includes a camming surface which interfaces with the first pivot unit and the second pivot unit, the camming surface being sized and structured to transform translational movement of the guide into pivotal movement of the first pivot unit and the second pivot unit.

17. A device for coupling at least one eyewear lens to at least one nasal applique attachable to a user's nose which results in dilation of a nasal passageway, the device comprising:
a base engageable with the at least one eyewear lens;
an eyewear frame including a forward frame element and a pair of arms pivotally coupled to the forward frame element, the base being integrally coupled to the forward frame element;
a first pivot unit coupled to the base and pivotable relative to the base about a first pivot axis; and
a second pivot unit coupled to the base and pivotable relative to the base about a second pivot axis;
the first pivot unit and the second pivot unit being interactable with at least one nasal applique to magnetically couple the first pivot unit and the second pivot unit to the at least one nasal applique, the magnetic coupling between the first pivot unit and the second pivot unit and the at least one nasal applique imparting a dilating force on the user's nose to dilate the nasal passageway when the at least one nasal applique is attached to the user's nose.

* * * * *